US012760060B2

(12) United States Patent
Micalizio

(10) Patent No.: US 12,760,060 B2
(45) Date of Patent: Oct. 13, 2026

(54) ANDROGEN RECEPTOR MODULATORS

(71) Applicant: TRUSTEES OF DARTMOUTH COLLEGE, Hanover, NH (US)

(72) Inventor: Glenn C. Micalizio, Norwich, VT (US)

(73) Assignee: TRUSTEES OF DARTMOUTH COLLEGE, Hanover, NH (US)

( * ) Notice: Subject to any disclaimer, the term of this patent is extended or adjusted under 35 U.S.C. 154(b) by 451 days.

(21) Appl. No.: 18/550,624

(22) PCT Filed: Mar. 14, 2022

(86) PCT No.: PCT/US2022/071130

§ 371 (c)(1),
(2) Date: Sep. 14, 2023

(87) PCT Pub. No.: WO2022/198191

PCT Pub. Date: Sep. 22, 2022

(65) Prior Publication Data

US 2024/0199683 A1 Jun. 20, 2024

Related U.S. Application Data

(60) Provisional application No. 63/161,112, filed on Mar. 15, 2021.

(51) Int. Cl.

| | |
|---|---|
| ***C07J 53/00*** | (2006.01) |
| ***A61K 31/568*** | (2006.01) |
| ***A61P 35/00*** | (2006.01) |

(52) U.S. Cl.

CPC .......... *C07J 53/008* (2013.01); *A61K 31/568* (2013.01); *A61P 35/00* (2018.01)

(58) Field of Classification Search

CPC .................................................... C07J 53/008

See application file for complete search history.

(56) References Cited

U.S. PATENT DOCUMENTS

| | | | |
|---|---|---|---|
| 11,459,353 | B2 | 10/2022 | Micalizio |
| 11,512,107 | B2 | 11/2022 | Micalizio |
| 11,787,835 | B2 | 10/2023 | Micalizio |
| 12,065,465 | B2 | 8/2024 | Micalizio |
| 2009/0176752 | A1 | 7/2009 | Lardy et al. |

FOREIGN PATENT DOCUMENTS

| | | | |
|---|---|---|---|
| WO | 2020051329 | A1 | 3/2020 |
| WO | 2021188415 | A1 | 9/2021 |
| WO | 2022198191 | A1 | 9/2022 |

OTHER PUBLICATIONS

Kim et al. CAS: 172: 62571, 2019.*

Kim, et al., A synthesis strategy for tetracyclic terpenoids leads to agonists of ERβ, Nature Communications, 10(1):2448, 2019.

Pospisil, Tomas, Cyclopropanes—novel methodologies for their preparation and applications. Doctoral Thesis, Abstract, pp. 79-82. 2011.

* cited by examiner

*Primary Examiner* — Rei Tsang Shiao

(74) *Attorney, Agent, or Firm* — Neal, Gerber & Eisenberg LLP

(57) ABSTRACT

The present disclosure relates to polycyclic (e.g., tetracyclic) androgen receptor (AR) modulators, synthetic methods for preparing such AR modulators, and methods of using such AR modulators to treat an androgen-dependent condition, such as prostate cancer or BPH. Exemplary compounds have quaternary centers at C10 and C13 and a fused cyclic ring comprising C14 and C15.

18 Claims, 14 Drawing Sheets

$^1$H NMR (500 MHz, Chloroform-d) 101:

$^{13}$C NMR (150 MHZ, Chloroform-d) 101:

$^1$H NMR (500 MHz, Chloroform-d) 102:

$^{13}$C NMR (150 MHz, Chloroform-d) 102:

$^{1}H$ NMR (500 MHz, Chloroform-d) 103:

$^{13}C$ NMR (150 MHz, Chloroform-d) 103:

$^1$H NMR (500 MHz, Chloroform-d) 104:

$^{13}$C NMR (150 MHz, Chloroform-d) 104:

$^{1}H$ NMR (500 MHz, Chloroform-d) 105:

$^{13}C$ NMR (150 MHz, Chloroform-d) 105:

$^1H$ NMR (500 MHz, Chloroform-d) 106:

$^{13}C$ NMR (150 MHz, Chloroform-d) 106:

$^1$H NMR (500 MHz, Chloroform-d) 107:

$^{13}$C NMR (150 MHz, Chloroform-d) 107:

$^{1}H$ NMR (500 MHz, Chloroform-d) 108:

$^{13}C$ NMR (150 MHz, Chloroform-d) 108:

$^{1}H$ NMR (500 MHz, Chloroform-d) 109:

$^{13}C$ NMR (150 MHz, Chloroform-d) 109:

$^1H$ NMR (500 MHz, Chloroform-d) 110:

$^{13}C$ NMR (150 MHz, Chloroform-d) 110:

ANDROGEN RECEPTOR MODULATORS

CROSS REFERENCE TO RELATED APPLICATIONS

This patent application is a National Stage Entry of International Application No. PCT/US2022/071130, filed on Mar. 14, 2022, which claims priority to U.S. Provisional Patent Application No. 63/161,112, filed on Mar. 15, 2021, the entire contents of which are fully incorporated herein by reference

FEDERALLY SPONSORED RESEARCH OR DEVELOPMENT

This invention was made with government support under R01 GM080266 awarded by the National Institutes of Health and R35 GM134725 awarded by the National Institutes of Health. The government has certain rights in the invention.

FIELD OF THE INVENTION

The present disclosure provides a new class of androgen receptor modulators and their use to treat androgen-dependent conditions, including androgen receptor-driven malignancies, such as prostate cancer.

BACKGROUND OF THE INVENTION

The Androgen Receptor (AR) is a ligand-dependent transcription factor composed of an N-terminal domain, a DNA binding domain, and a C-terminal domain. The C-terminal domain includes a ligand binding domain (LBD). The AR is activated by androgen binding, which exposes the nuclear localization signal (NLS) thereby initiating translocation of the complex into the nucleus to exert transcriptional activity.

Several medical conditions are known to be dependent on, or sensitive to, the presence of androgenic activity. Such androgen-dependent conditions include acne, seborrhea, androgenic alopecia, hirsutism, hidradenitis suppurativa, precocious puberty in boys, hypersexuality, paraphilias, benign prostatic hyperplasia (BPH), prostate cancer, and hyperandrogenism in women such as in polycystic ovary syndrome (PCOS).

Prostate cancer is one of the most common cancers in men. Each year in the United States alone, nearly 200,000 new cases of prostate cancer will be diagnosed and about 33,000 deaths will be attributed to prostate cancer. It has been estimated that about 1 in 9 men will be diagnosed with prostate cancer during his lifetime.

Prostate cancer develops in the prostate and is typically slow growing; however, some prostate cancers are aggressive. Prostate cancer cells are typically androgen-dependent and may metastasize from the prostate to other parts of the body, particularly the bones and lymph nodes.

Thus, there remains a need for compounds that modulate androgen receptor activity and, particularly, androgen receptor modulators that possess anti-androgen properties.

SUMMARY OF THE INVENTION

The present disclosure relates to polycyclic (e.g., tetracyclic) compounds, including compounds that serve as androgen receptor modulators. In certain embodiments, the compounds have a C19 steroidal scaffold. In other embodiments, compounds having a C19 steroidal scaffold enable access to further compounds based on, or derived from, the C19 scaffold. In certain embodiments, the compounds are C9-α-alkyl as well as C13-β-alkyl steroidal tetracycles. In certain embodiments, the compounds are C10-β-alkyl as well as C13-β-alkyl steroidal tetracycles. In some such embodiments, the compounds further comprise a C14,C15-alkylene (e.g., methylene) bridge. In some such embodiments, the compounds comprise a C14,C15-α-alkylene bridge.

The present disclosure also relates to the use of such compounds as biologically active (e.g., therapeutic) components in, for example, pharmaceutical compositions and/or directly as human and/or animal therapeutics and medicines. In certain embodiments, the compounds are androgen receptor antagonists and/or may be used to treat or prevent androgen-dependent conditions, including proliferative diseases such as prostate cancer or BPH.

In one aspect, this disclosure provides a method for treating an androgen-dependent condition by administering a compound disclosed herein or a pharmaceutically acceptable salt or prodrug thereof to a patient in need thereof. In some embodiments, the compound is selected from Compounds 101-110 and Compounds 201-204. In some embodiments, the androgen-dependent condition is prostate cancer or BPH. In some embodiments, the compound is administered orally.

The compounds, pharmaceutical compositions comprising the compounds, and methods for treating or preventing conditions, disorders, or diseases by administering the compounds are further described herein.

These and other objects of the invention are described in the following paragraphs. These objects should not be deemed to narrow the scope of the invention.

BRIEF DESCRIPTION OF THE DRAWINGS

For a better understanding of the invention, reference may be made to embodiments shown in the following drawings. The components in the drawings are not necessarily to scale and related elements may be omitted, or in some instances proportions may have been exaggerated, so as to emphasize and clearly illustrate the novel features described herein. In addition, system components can be variously arranged, as known in the art.

DESCRIPTION OF THE INVENTION

Figure 1:
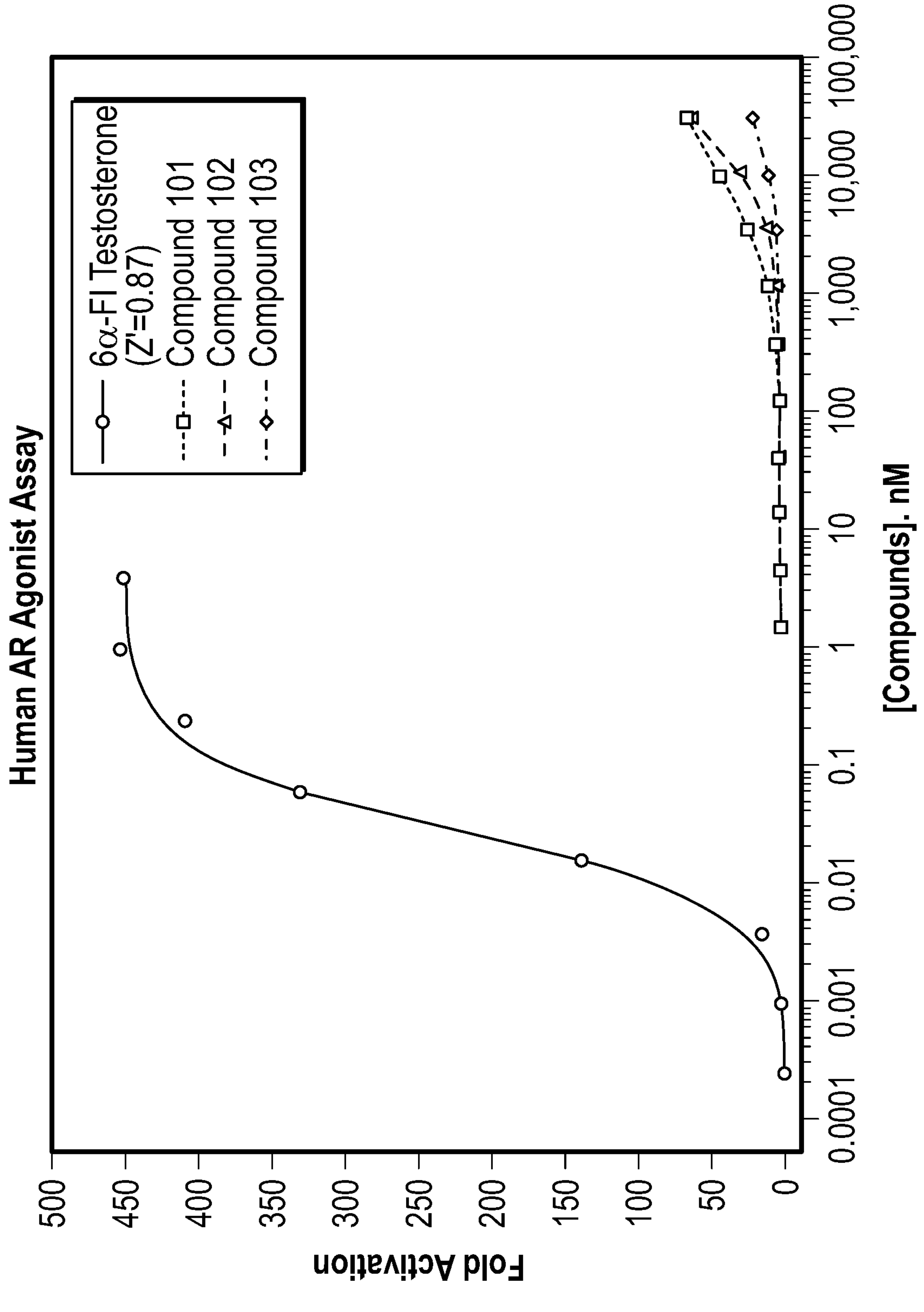
FIG. 1 is a line graph showing the results of a human AR agonist assay for 6α-fluorotestosterone and Compounds 101, 102, and 103.

This detailed description is intended only to acquaint others skilled in the art with the present invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

In certain aspects, the present disclosure relates to compounds (and methods of making such compounds, compositions comprising such compounds, and methods of using such compounds) comprising a generic tetracyclic steroidal (A, B, C, D) ring structure, as follows:

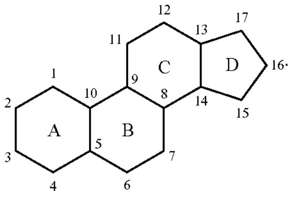

Each carbon ring atom of the generic tetracyclic steroidal ring structure is numbered according to the numbering convention for steroid molecules, which is known in the art and has been explained, for example, in Moss G. P. *Nomenclature of Steroids*, Pure & Appl. Chem., 61 (10) 1783-1822 (1989), which is hereby incorporated by reference in its entirety. Particular carbon atoms in the structures of the various disclosed formulas are referred to herein by "C" number, for example, C1, C2, C3, C9, C10, C13, etc. The number is reserved to a particular position in that parent skeletal structure whether that position is occupied by a carbon atom or not.

More particularly, the present disclosure relates to compounds (and methods of making such compounds, compositions comprising such compounds, and methods of using such compounds) comprising a generic C19 steroidal core skeleton of according to the following formulas, where additional substitution about these base structures is intended to be within the scope of the invention:

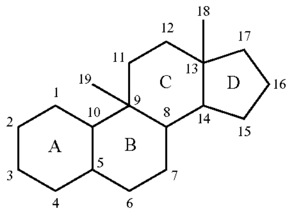

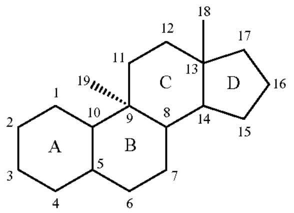

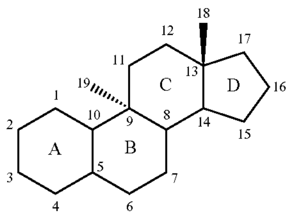

-continued

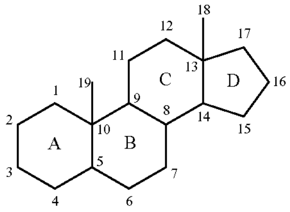

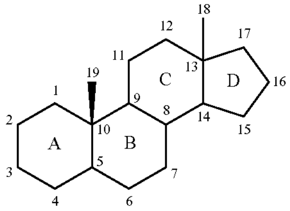

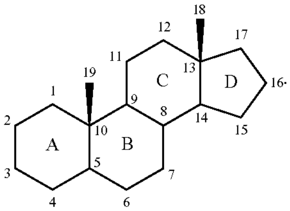

In one aspect, this disclosure provides compounds having a chemical structure including a C19 steroidal core skeleton, said C19 steroidal core skeleton having a quaternary center at each of carbon C9 and carbon C13. In certain embodiments, the "C19" group attached at C9 projects an electron density beyond the traditional bounds of the androgen receptor ligand binding pocket. In some such embodiments, the "C19" group is attached at C9α, where the bond is shown as .

The C19 steroidal core skeleton depicted above encompasses, inter alia, a C20 steroidal core skeleton, such as:

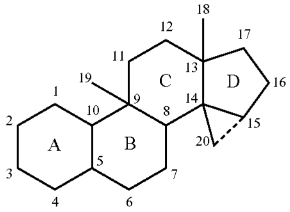

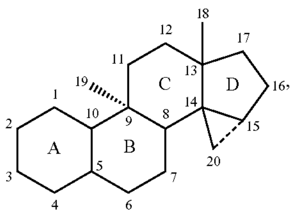 or

-continued

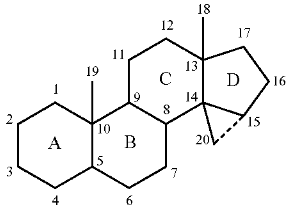

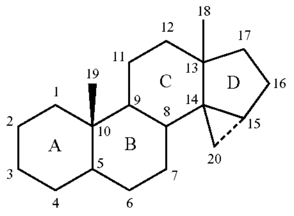

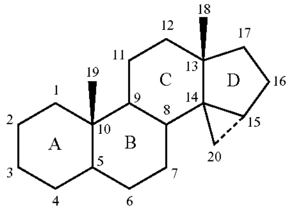

where the dashed bond between C15 and C20 represents an optional bond forming a fused cyclopropane.

By way of example, the C19 steroidal core skeleton depicted above encompasses, inter alia, a steroidal core skeleton, such as:

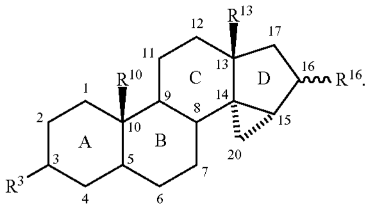

The numbering convention throughout the present disclosure is in accordance with numbered structures above.

In reference to the generic tetracyclic steroidal (A, B, C, D) ring structure and the generic C19 and C20 steroidal core skeletons, it will be well appreciated that in view of the disclosure contained herein as well as the teachings in the relevant fields of art, the compounds, compositions, and methods of the present disclosure are not limited to any particular respective constituent (R) group(s) at the various numbered carbon atoms. For example, an R group may be hydrogen, a $C_{1-10}$-aliphatic group, a $C_{6-10}$ aromatic group, carboxylic acid, carboxylic acid ester, hydroxyl, or halogen. Moreover, it will be well appreciated that in view of the disclosure contained herein as well as the teachings in the relevant fields of art, the compounds, compositions, and methods of the present disclosure may comprise ones in which any of the rings (A, B, C, D) can be saturated, partially unsaturated, or completely unsaturated (i.e., aromatic); in particular, the A ring can be saturated, partially unsaturated, or completely unsaturated; the B ring can be saturated or partially unsaturated; the C ring can be saturated or partially unsaturated; and the D ring can be saturated or partially unsaturated.

Thus, the C19 steroidal core skeleton depicted above also encompasses, inter alia, a steroidal core skeleton, such as:

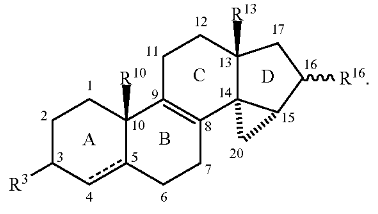

In an exemplary embodiment, with reference to any of the above formulae, each of C1, C2, C4, C6, C7, C11, C12, and C17 is independently substituted with hydrogen, $C_{1-10}$-alkyl, $C_{2-10}$-alkenyl, $C_{2-10}$-alkynyl, $C_{1-10}$-haloalkyl, halogen, oxo, hydroxy, $C_{1-6}$-alkoxy, —O—$C_{1-10}$-alkyl, —O—$C_{2-10}$-alkenyl, —O—$C_{2-10}$-alkynyl, —O—$C_{1-10}$-haloalkyl, —O—$C_{6-10}$-aryl, —O-5- to 10-membered heteroaryl, —OC(O)—$C_{1-10}$-alkyl, —OC(O)—$C_{6-10}$-aryl, —OC(O)-5- to 10-membered heteroaryl, $C_{6-10}$-aryl, or 5- to 10-membered heteroaryl and $R^3$, $R^{10}$, $R^{13}$, and $R^{16}$ are defined herein.

A. Definitions

As used in the specification and the appended claims, unless specified to the contrary, the following terms have the meaning indicated:

The term "about" as used herein means approximately, and in most cases within 10% of the stated value.

The term "aliphatic" as used herein includes both saturated and unsaturated, nonaromatic, straight chain (i.e., unbranched), branched, acyclic, and cyclic (i.e., carbocyclic) hydrocarbons. In some embodiments, an aliphatic group is optionally substituted with one or more functional groups. In some embodiments, one or more units (e.g., methylene units) of an aliphatic may be replaced with —O—, —$NR^Z$—, —C(O)—, —C(O)O—, —OC(O)—, —C(O)$NR^Z$—, —$NR^Z$C(O)—, —$S(O)_y$—, —$S(O)_yNR^Z$—, —$NR^ZS(O)_y$—, —C(S)$NR^Z$—, or —$NR^Z$C(S)—, where $R^Z$ is hydrogen, $C_{1-6}$-alkyl, $C_{1-6}$-haloalkyl, $C_{2-6}$-alkenyl, $C_{2-6}$-haloalkenyl, $C_{2-6}$-alkynyl, $C_{2-6}$-haloalkynyl, $C_{3-7}$-cycloalkyl, and y is 0, 1, or 2. As will be appreciated by one of ordinary skill in the art, "aliphatic" is intended herein to include alkyl, alkenyl, alkynyl, cycloalkyl, and cycloalkenyl moieties.

The term "alkyl" as used herein includes linear or branched saturated aliphatic hydrocarbon groups having the specified number of carbon atoms. $C_{1-6}$-alkyl, for example, includes $C_1$, $C_2$, $C_3$, $C_4$, $C_5$, and $C_6$ alkyl groups. Examples of alkyl include, but are not limited to, methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl. In particular embodiments, an alkyl of this invention is a $C_{1-10}$-alkyl, $C_{1-9}$-alkyl, $C_{1-8}$-alkyl, $C_{1-7}$-alkyl, $C_{1-6}$-alkyl, $C_{1-5}$-alkyl, $C_{1-4}$-alkyl, $C_{1-3}$-alkyl, or $C_{1-2}$ alkyl.

The term "pharmaceutically acceptable" is used adjectivally to mean that the modified noun is appropriate for use as a pharmaceutical product for human use or as a part of a pharmaceutical product for human use.

The term “prodrug” refers to a compound that can be readily converted (e.g., metabolized) in vivo to yield a parent compound. Prodrugs include, but are not limited to, compounds having a substituent, such an ester moiety, attached to a hydroxy group at C3 (steroid numbering), which yield a parent compound having a phenolic A ring upon in vivo conversion. Suitable C3 substituents are identified in US2007/0015740 A1, which is herein incorporated by reference in its entirety. Exemplary ester moieties include, but are not limited to, an alkyl ester (e.g., —O—$C_{1-6}$-alkyl), a carbonate ester (e.g., —O—C(O)—O—$C_{1-10}$-alkyl), a carbamate ester (e.g., —O—C(O)—$NR^{Z1}R^{Z2}$), and a sulfamate ester (e.g., —O—$S(O)_2NR^{Z1}R^{Z2}$). Additionally or alternatively, prodrugs may have a substituent, such as an optionally substituted 5- to 10-membered heteroaryl, attached to carbon C17 (steroid numbering), such as those identified in US2014/0371181 A1, which is herein incorporated by reference in its entirety. Prodrugs also include, but are not limited to, di-steroidal prodrugs such as those disclosed in U.S. Pat. No. 7,067,505, which is herein incorporated by reference in its entirety.

The terms “treat”, “treating” and “treatment” refer to a method of alleviating or abrogating a condition, disorder, or disease and/or the attendant symptoms thereof.

B. Compounds

In one aspect, compounds disclosed herein possess biological activity, for example, as a modulator of the androgen receptor. In some such embodiments, compounds disclosed herein possess potent anti-androgenic activity while substantially lacking agonistic activity. In another aspect, compounds disclosed herein provide a platform for development of analogs or derivatives possessing biological activity, for example, as modulators of the androgen receptor. Thus, in certain embodiments, a compound disclosed herein may be transformed by methods well known to those skilled in the art of synthetic organic chemistry into a derivative compound that possesses biological activity, for example, as a modulator of the androgen receptor.

In one aspect, compounds disclosed herein comprise a steroidal core, such as a C19 steroidal core. In certain embodiments, such compounds comprise an aliphatic group attached at C9 and positioned on the alpha (α) face. In some such embodiments, the aliphatic group attached at C9α projects an electron density beyond the traditional bounds of the androgen receptor ligand binding pocket. In certain embodiments, such compounds comprise a C8-C14 double bond in the C ring. In certain embodiments, such compounds comprise an alcohol or other group attached at C16 (rather than the typical C17 alcohol in other anti-androgen agents). In certain embodiments, such compounds comprise a C4-C5 double bond in the A ring. In particularly preferred embodiments, the compounds comprise an aliphatic group attached at C9α that projects an electron density beyond the traditional bounds of the androgen receptor ligand binding pocket, a C8-C14 double bond in the C ring, and an alcohol moiety attached at C16. In other particularly preferred embodiments, the compounds comprise an aliphatic group attached at C9α that projects an electron density beyond the traditional bounds of the androgen receptor ligand binding pocket, a C4-C5 double bond in the A ring, a C8-C14 double bond in the C ring, and an alcohol moiety attached at C16. Such compounds unexpectedly act as androgen receptor antagonists In certain embodiments, the compounds, with reference to the quaternary centers at C9 and C13, are anti-isomers (the quaternary center at C9 projects a substituent on the opposite face of the tetracycle as the substituent at C13). For example, the compounds may be C9-α-substituted and C13-β-substituted or, alternatively, C9-β-substituted and C13-α-substituted.

Exemplary generic formula include:

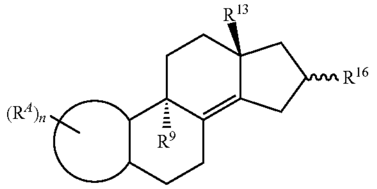

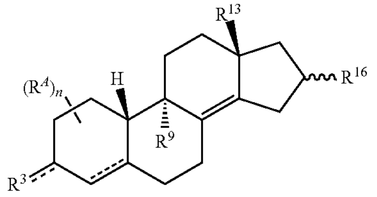

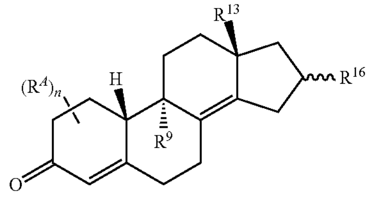

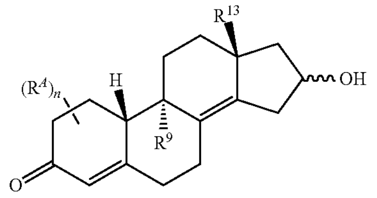

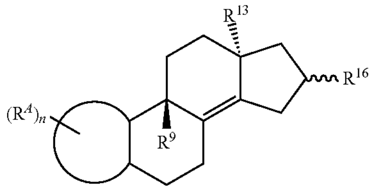

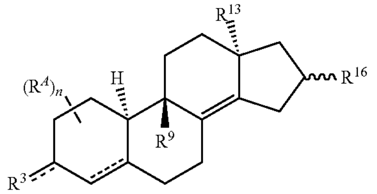

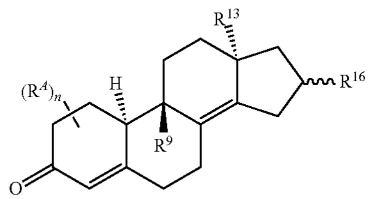

-continued

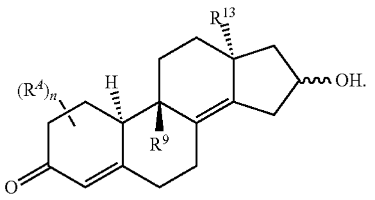

In certain embodiments, the $R^{16}$ or —OH substituent attached to carbon C16 by  has the alpha orientation (e.g., 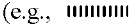). In certain other embodiments the $R^{16}$ or —OH substituent attached to carbon C16 by 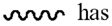 has the beta orientation (e.g., ). In some such embodiments, $R^{16}$ is oxo. In some such embodiments, $R^{16}$ is —$OR^D$, such as —OH.

In one aspect, compounds disclosed herein comprise a steroidal core, such as a C19 steroidal core. In certain embodiments, such compounds comprise an alcohol or other group attached at C16 (rather than the typical C17 alcohol in other anti-androgen agents). In certain embodiments, such compounds comprise a fused carbocyclic ring that includes C14 and C15 of the steroidal core. In certain embodiments, such compounds comprise a C4-C5 single bond in the A ring. In particularly preferred embodiments, the compounds comprise an alcohol moiety attached at C16 and a vinyl cyclopropane including C14-C15. In other particularly preferred embodiments, the compounds comprise an alcohol moiety attached at C16, a vinyl cyclopropane including C14-C15, and a C4-C5 single bond in the A ring. Such compounds unexpectedly act as androgen receptor antagonists.

In certain embodiments, the compounds comprise a trans-ring fusion of the C and D rings, such that the quaternary center at C13 projects a substituent on the opposite face of the tetracycle as the fused carbocyclic ring that includes C14 and C15.

In certain embodiments, the compounds, with reference to the quaternary centers at C10 and C13, are syn-isomers (the quaternary center at C10 projects a substituent on the same face of the tetracycle as the substituent at C13). For example, the compounds may be C10-β-substituted and C10-β-substituted or, alternatively, C10-α-substituted and C13-α-substituted.

Exemplary generic formula include:

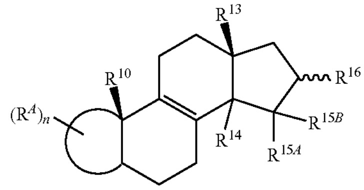

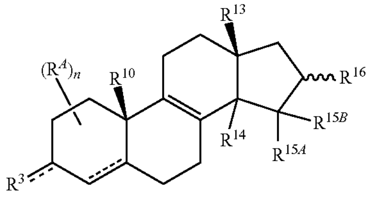

-continued

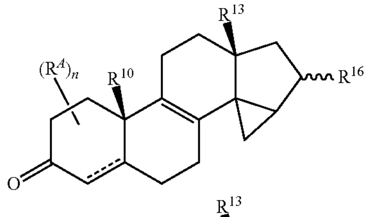

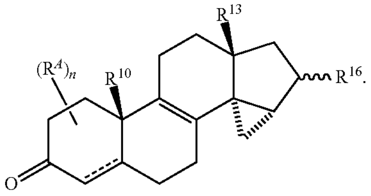

In certain embodiments, the $R^{16}$ substituent attached to carbon C16 by  has the alpha orientation (e.g., ). In certain other embodiments the $R^{16}$ substituent attached to carbon C16 by  has the beta orientation (e.g., ). In some such embodiments, $R^{16}$ is oxo. In some such embodiments, $R^{16}$ is —$OR^D$, such as —OH.

In one aspect, this disclosure provides a compound or a salt thereof, wherein the compound either has a structure corresponding to Formula (I-A) or Formula (I-B):

(I-A)

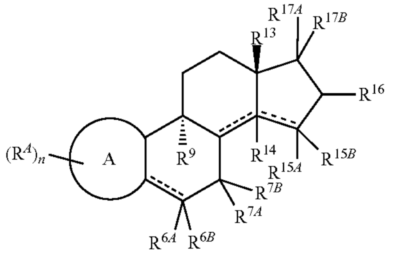

or (I-B)

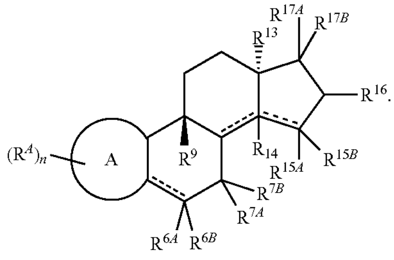

The compounds of Formula (I-A) and Formula (I-B) optionally include a double bond between carbon C8 and carbon C14 (i.e., 8,14-unsaturated) or, alternatively, a double bond between carbon C14 and carbon C15, provided that if the bond between carbon C8 and carbon C14 or the bond between carbon C14 and carbon C15 is a double bond, then $R^{14}$ is absent and provided that if the bond between carbon C14 and carbon C15 is a double bond, then one of $R^{15A}$ or $R^{15B}$ is absent.

The compounds of Formula (I-A) and Formula (I-B) optionally include a double bond between carbon C5 and carbon C6 (i.e., 5,6-unsaturated), provided that if the bond between carbon C5 and carbon C6 is a double bond, then one of $R^{6A}$ or $R^{6B}$ is absent.

In certain embodiments, the compound has a structure corresponding to Formula (I-A1) or Formula (I-B1):

(I-A1)

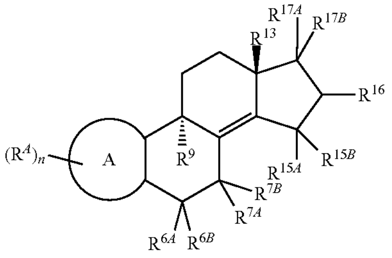

or (I-B1)

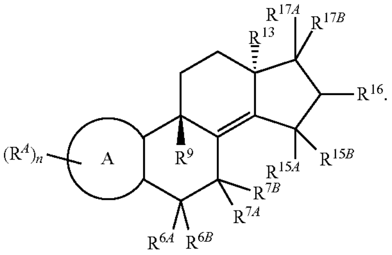

In one aspect, this disclosure provides a compound or a salt thereof, wherein the compound either has a structure corresponding to Formula (II-A) or Formula (II-B):

(II-A)

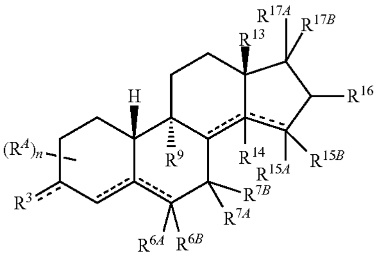

or (II-B)

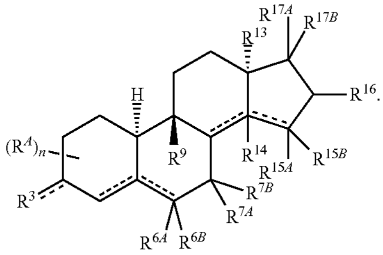

The compounds of Formula (II-A) and Formula (II-B) optionally include a double bond between carbon C8 and carbon C14 (i.e., 8,14-unsaturated) or, alternatively, a double bond between carbon C14 and carbon C15, provided that if the bond between carbon C8 and carbon C14 or the bond between carbon C14 and carbon C15 is a double bond, then $R^{14}$ is absent and provided that if the bond between carbon C14 and carbon C15 is a double bond, then one of $R^{15A}$ or $R^{15B}$ is absent.

The compounds of Formula (II-A) and Formula (II-B) optionally include a double bond between carbon C4 and carbon C5 (i.e., 4,5-unsaturated) or, alternatively, a double bond between carbon C5 and carbon C6, provided that if the bond between carbon C5 and carbon C6 is a double bond, then one of $R^{6A}$ or $R^{6B}$ is absent.

In certain embodiments, the compound has a structure corresponding to Formula (II-A1), Formula (II-A1.1), Formula (II-A1.2), Formula (II-A1.3), Formula (II-B1), Formula (II-B1.1), Formula (II-B1.2), or Formula (II-B1.3):

(II-A1)

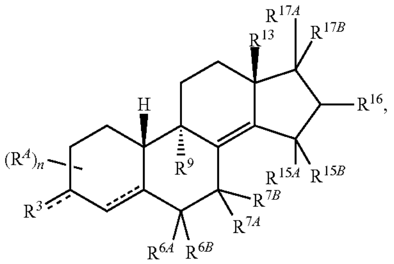

(II-B1)

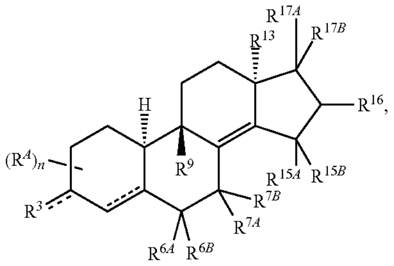

(II-A1.1)

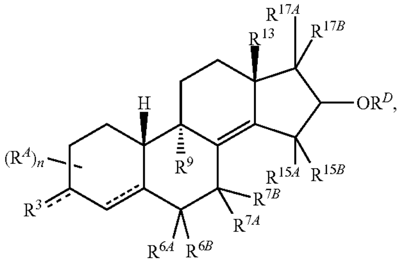

(II-B1.1)

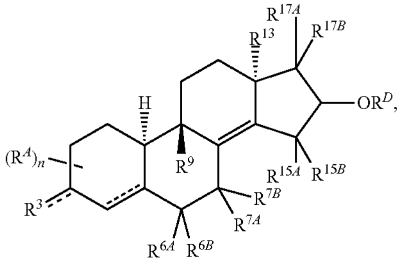

(II-A1.2)

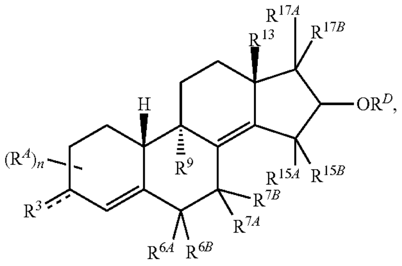

-continued (II-B1.2)

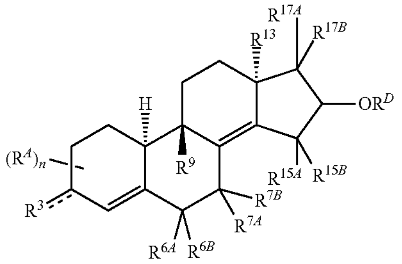

(II-A1.3)

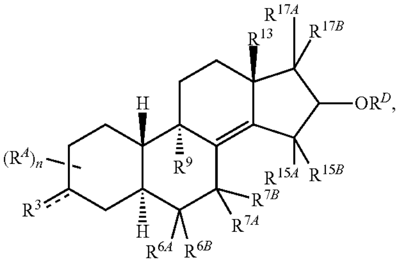

or (II-B1.3)

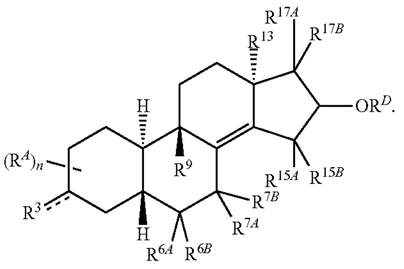

In one aspect, this disclosure provides a compound or a salt thereof, wherein the compound either has a structure corresponding to Formula (III-A) or Formula (III-B):

(III-A)

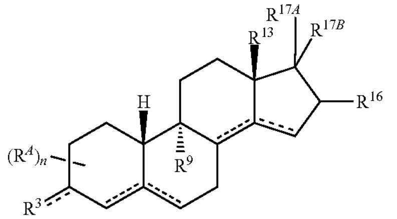

or (III-B)

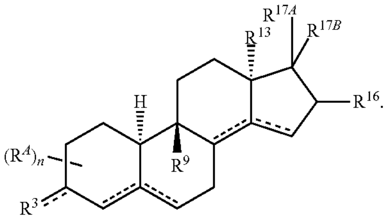

The compounds of Formula (III-A) and Formula (III-B) optionally include a double bond between carbon C8 and carbon C14 (i.e., 8,14-unsaturated) or, alternatively, a double bond between carbon C14 and carbon C15. The compounds of Formula (III-A) and Formula (III-B) optionally include a double bond between carbon C4 and carbon C5 (i.e., 4,5-unsaturated) or, alternatively, a double bond between carbon C5 and carbon C6.

In certain embodiments, the compound has a structure corresponding to Formula (III-A1), Formula (III-A1.1), Formula (III-A1.2), Formula (III-A1.3), Formula (III-B1), Formula (III-B1.1), Formula (III-B1.2), or Formula (III-B1.3):

(III-A1)

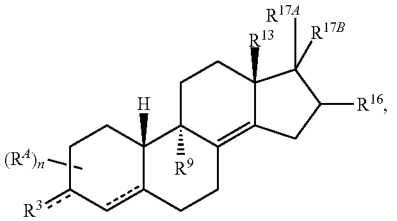

(III-B1)

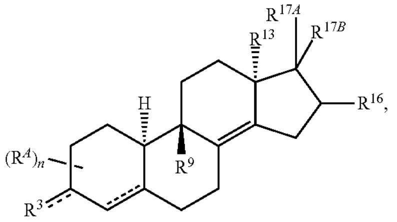

(III-A1.1)

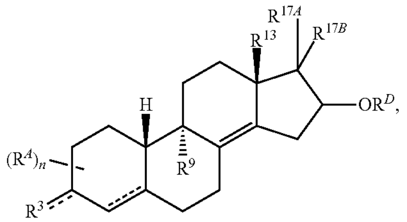

(III-B1.1)

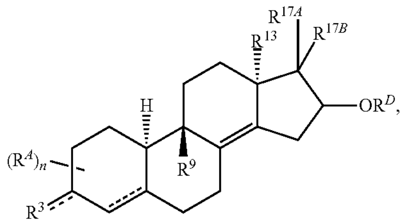

(III-A1.2)

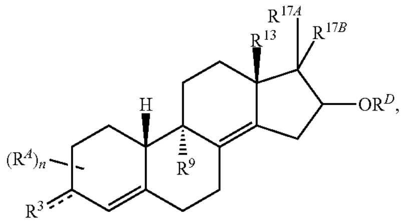

(III-B1.2)

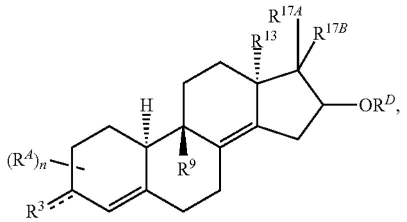

-continued (III-A1.3)

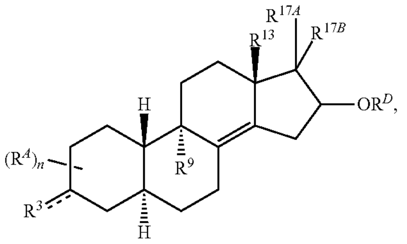

or (III-B1.3)

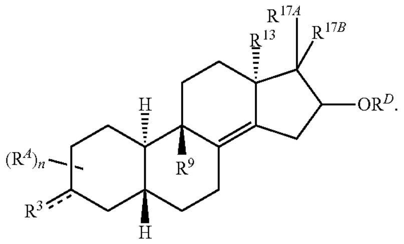

In one aspect, this disclosure provides a compound or a salt thereof, wherein the compound either has a structure corresponding to Formula (IV-A) or Formula (IV-B):

(IV-A)

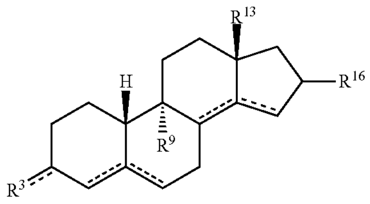

or (IV-B)

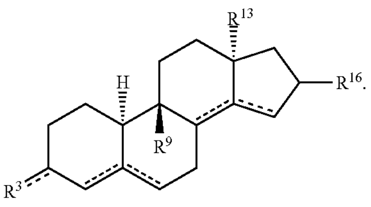

The compounds of Formula (IV-A) and Formula (IV-B) optionally include a double bond between carbon C8 and carbon C14 (i.e., 8,14-unsaturated) or, alternatively, a double bond between carbon C14 and carbon C15. The compounds of Formula (IV-A) and Formula (IV-B) optionally include a double bond between carbon C4 and carbon C5 (i.e., 4,5-unsaturated) or, alternatively, a double bond between carbon C5 and carbon C6.

In certain embodiments, the compound has a structure corresponding to Formula (IV-A1), Formula (IV-A1.1), Formula (IV-A1.2), Formula (IV-A1.3), Formula (IV-B1), Formula (IV-B1.1), Formula (IV-B1.2), or Formula (IV-B1.3):

(IV-A1)

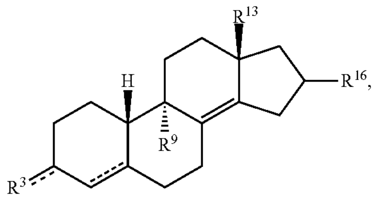

(IV-B1)

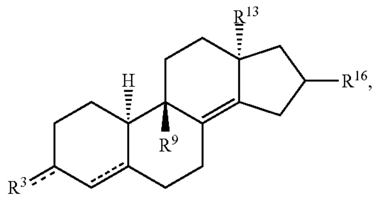

(IV-A1.1)

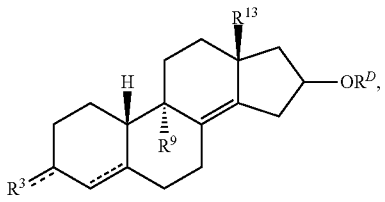

(IV-B1.1)

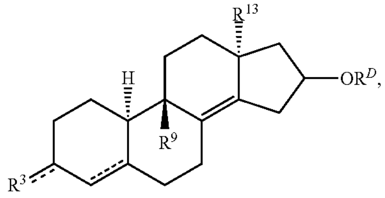

(IV-A1.2)

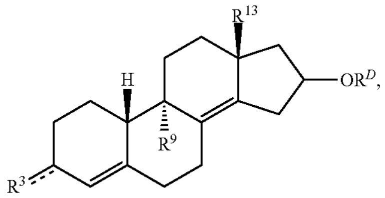

(IV-B1.2)

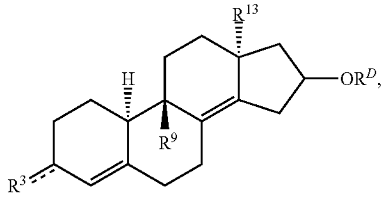

(IV-A1.3)

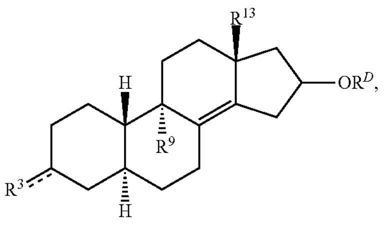

or

-continued (IV-B1.3)

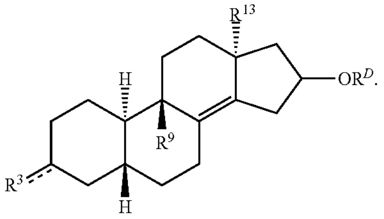

In one aspect, this disclosure provides a compound or a salt thereof, wherein the compound has a structure corresponding to Formula (V-A), Formula (V-B), Formula (V-C), or Formula (V-D):

(V-A)

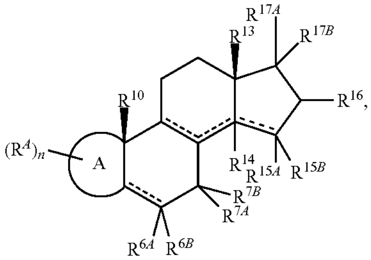

(V-B)

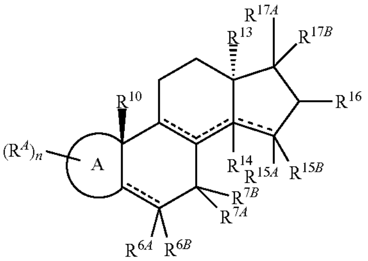

(V-C)

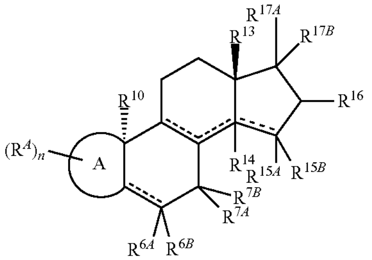

or (V-D)

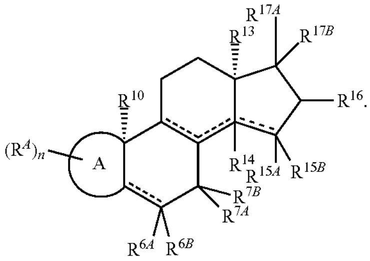

The compounds of Formula (V-A), Formula (V-B), Formula (V-C), and Formula (V-D) optionally include a double bond between carbon C8 and carbon C9 (i.e., 8,9-unsaturated) or, alternatively, a double bond between carbon C8 and carbon C14 (i.e., 8,14-unsaturated) or, alternatively, a double bond between carbon C14 and carbon C15, provided that if the bond between carbon C8 and carbon C14 or the bond between carbon C14 and carbon C15 is a double bond, then $R^{14}$ is absent and provided that if the bond between carbon C14 and carbon C15 is a double bond, then one of $R^{15A}$ or $R^{15B}$ is absent.

The compounds of Formula (V-A), Formula (V-B), Formula (V-C), and Formula (V-D) optionally include a double bond between carbon C5 and carbon C6, provided that if the bond between carbon C5 and carbon C6 is a double bond, then one of $R^{6A}$ or $R^{6B}$ is absent.

In certain embodiments, the compound has a structure corresponding to Formula (V-A1), Formula (V-B1), Formula (V-C1), or Formula (V-D1):

(V-A1)

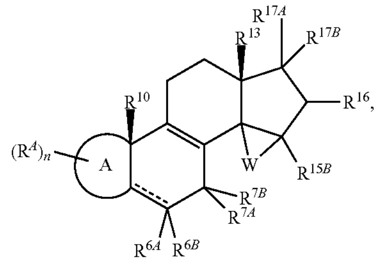

(V-B1)

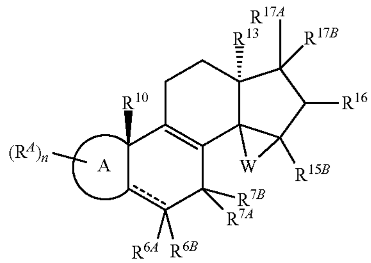

(V-C1)

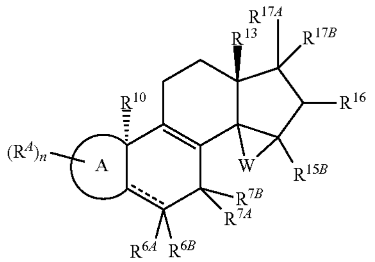

or (V-D1)

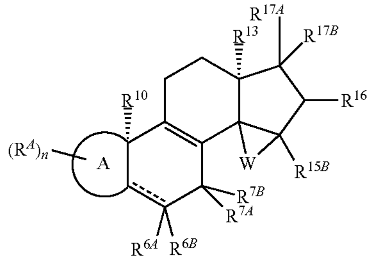

wherein W, together with carbon atoms C14 and C15, forms a $C_3$-$C_7$-carbocycle or a 3- to 7-membered heterocycle and wherein the $C_3$-$C_7$-carbocycle or 3- to 7-membered heterocycle is optionally substituted with one or more halogen, hydroxy, $C_{1-6}$-alkyl, $C_{1-6}$-haloalkyl, or $C_{1-6}$-alkoxy.

In certain embodiments, the compound has a structure corresponding to Formula (V-A2), Formula (V-B2), Formula (V-C2), or Formula (V-D2):

(V-A1)

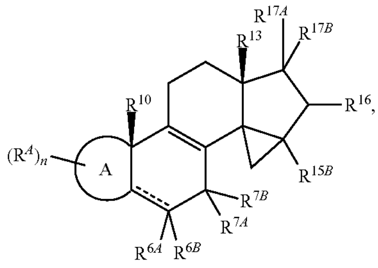

(V-B2)

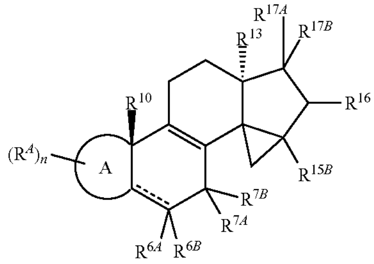

(V-C2)

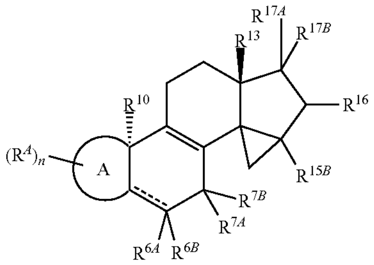

or (V-D2)

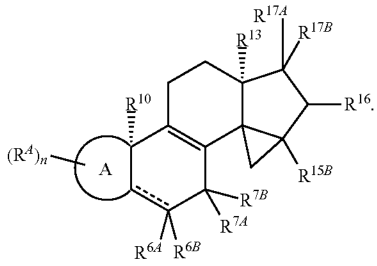

In one aspect, this disclosure provides a compound or a salt thereof, wherein the compound has a structure corresponding to Formula (VI-A), Formula (VI-B), Formula (VI-C), or Formula (VI-D):

(VI-A)

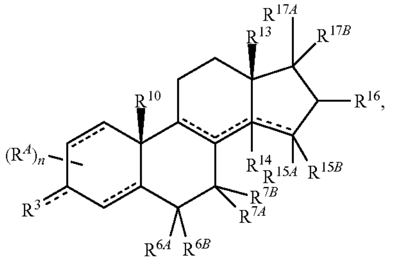

-continued (VI-B)

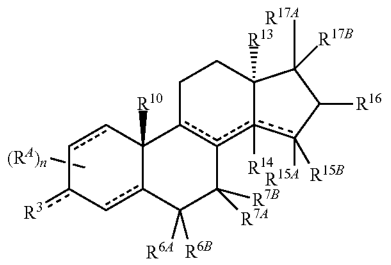

(VI-C)

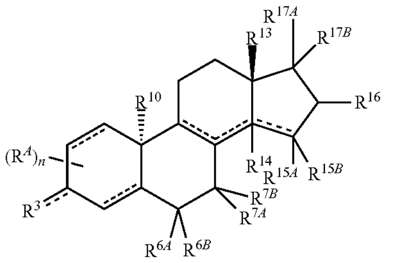

or (VI-D)

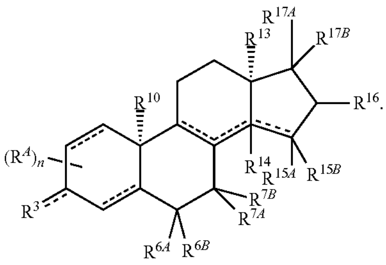

The compounds of Formula (VI-A), Formula (VI-B), Formula (VI-C), and Formula (VI-D) optionally include a double bond between carbon C8 and carbon C9 (i.e., 8,9-unsaturated) or, alternatively, a double bond between carbon C8 and carbon C14 (i.e., 8,14-unsaturated) or, alternatively, a double bond between carbon C14 and carbon C15, provided that if the bond between carbon C8 and carbon C14 or the bond between carbon C14 and carbon C15 is a double bond, then $R^{14}$ is absent and provided that if the bond between carbon C14 and carbon C15 is a double bond, then one of $R^{15A}$ or $R^{15B}$ is absent.

In certain embodiments, the compound has a structure corresponding to Formula (VI-A1), Formula (VI-B1), Formula (VI-C1), or Formula (VI-D1):

(VI-A1)

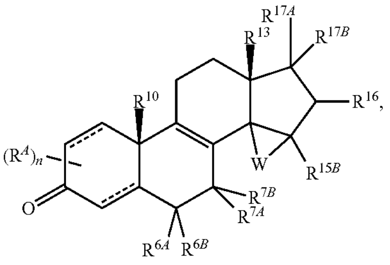

-continued (VI-B1)

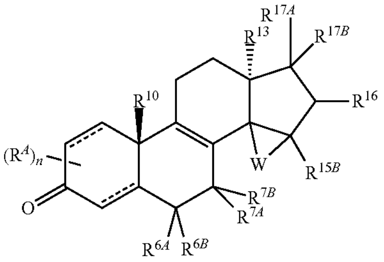

(VI-C1)

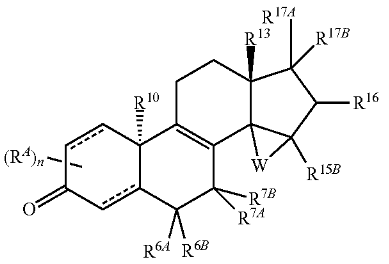

or (VI-D1)

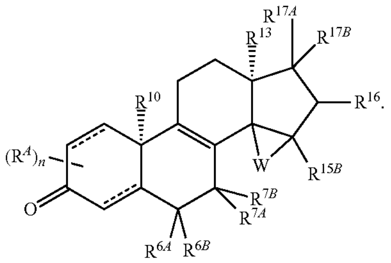

wherein W, together with carbon atoms C14 and C15, forms a $C_3$-$C_7$-carbocycle or a 3- to 7-membered heterocycle and wherein the $C_3$-$C_7$-carbocycle or 3- to 7-membered heterocycle is optionally substituted with one or more halogen, hydroxy, $C_{1-6}$-alkyl, $C_{1-6}$-haloalkyl, or $C_{1-6}$-alkoxy.

In certain embodiments, the compound has a structure corresponding to Formula (VI-A2), Formula (VI-B2), Formula (VI-C2), or Formula (VI-D2):

(VI-A2)

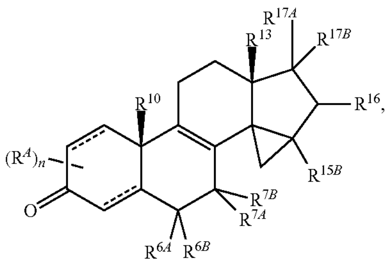

(VI-B2)

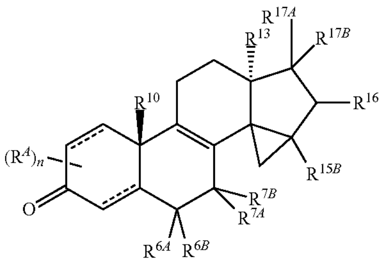

-continued (VI-C2)

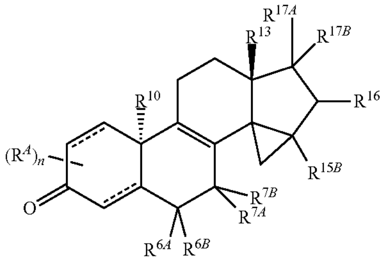

or (VI-D2)

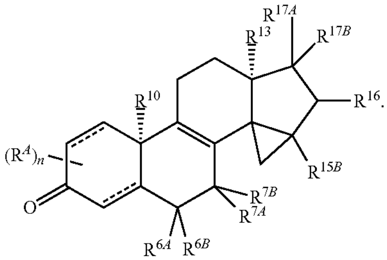

In certain embodiments, the compounds of Formula (VI-A), Formula (VI-B), Formula (VI-C), and Formula (VI-D) comprise a double bond between carbon C1 and carbon C2. In some such embodiments, the bond between carbon C4 and carbon C5 is also a double bond.

In certain embodiments, the compounds of Formula (VI-A), Formula (VI-B), Formula (VI-C), and Formula (VI-D) comprise a single bond between carbon C1 and carbon C2. In some such embodiments, the bond between carbon C4 and carbon C5 is a double bond.

In certain embodiments, the compounds of Formula (VI-A), Formula (VI-B), Formula (VI-C), and Formula (VI-D) comprise a double bond between carbon C4 and carbon C5. In some such embodiments, $R^{16}$ represents a hydroxy group or a $C_{1-6}$-alkoxy group.

In certain embodiments, the compounds of Formula (VI-A), Formula (VI-B), Formula (VI-C), and Formula (VI-D) comprise a single bond between carbon C4 and carbon C5. In some such embodiments, $R^{16}$ represents a hydroxy group or a $C_{1-6}$-alkoxy group.

In certain embodiments, the compound has a structure corresponding to Formula (VIa-A2), Formula (VIa-B2), Formula (VIa-C2), or Formula (VIa-D2):

(VIa-A2)

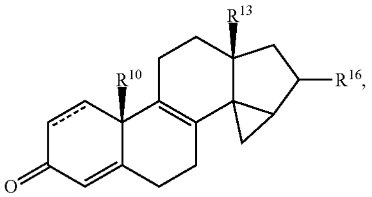

(VIa-B2)

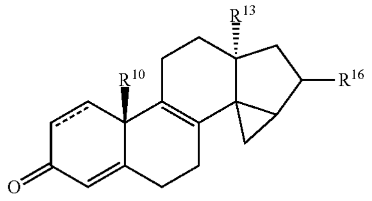

-continued (VIa-C2)

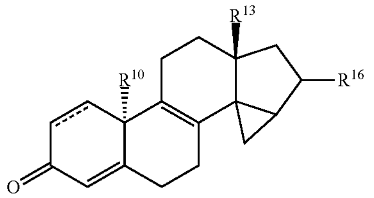

or (VIa-D2)

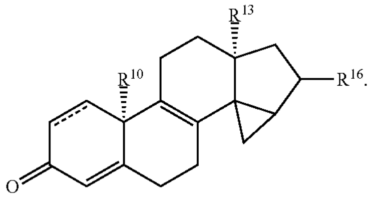

In certain embodiments, the compounds of Formula (VIa-A), Formula (VIa-B), Formula (VIa-C), and Formula (VIa-D) comprise a single bond between carbon C4 and carbon C5

In certain embodiments, the compounds of Formula (VIa-A), Formula (VIa-B), Formula (VIa-C), and Formula (VIa-D) comprise a double bond between carbon C4 and carbon C5.

In certain embodiments, $R^{10}$ is selected from the group consisting of $C_{1-14}$-alkyl and $C_{1-14}$-haloalkyl. In some such embodiments, $R^{10}$ is selected from the group consisting of $C_{1-6}$-alkyl and $C_{1-6}$-haloalkyl; alternatively, $R^{10}$ is selected from the group consisting of hydrogen, $C_{1-3}$-alkyl, and $C_{1-3}$-haloalkyl.

In certain embodiments, $R^{13}$ is selected from the group consisting of $C_{1-14}$-alkyl and $C_{1-14}$-haloalkyl. In some such embodiments, $R^{13}$ is selected from the group consisting of $C_{1-6}$-alkyl and $C_{1-6}$-haloalkyl.

In certain embodiments, $R^{16}$ is an oxo or —$OR^D$, wherein $R^D$ is selected from the group consisting of hydrogen, $C_{1-10}$-alkyl, and $C_{1-10}$-haloalkyl. In some such embodiments, $R^D$ is selected from the group consisting of hydrogen, $C_{1-6}$-alkyl, and $C_{1-6}$-haloalkyl; alternatively, $R^D$ is selected from the group consisting of hydrogen, $C_{1-3}$-alkyl, and $C_{1-3}$-haloalkyl. In some such embodiments, $R^{16}$ is an oxo or a hydroxy group.

In certain embodiments, the compounds of Formula (VI-A), Formula (VI-B), Formula (VI-C), and Formula (VI-D) comprise a single bond between carbon C4 and carbon C5. In some such embodiments, $R^{16}$ represents a hydroxy group or a $C_{1-6}$-alkoxy group.

In one aspect, this disclosure provides a compound or a salt thereof, wherein the compound has a structure corresponding to Formula (VII-A), Formula (VII-B), Formula (VII-C), or Formula (VII-D):

(VII-A)

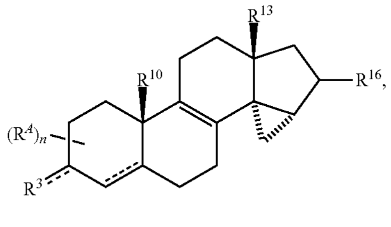

-continued (VII-B)

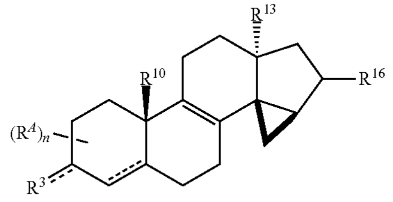

(VII-C)

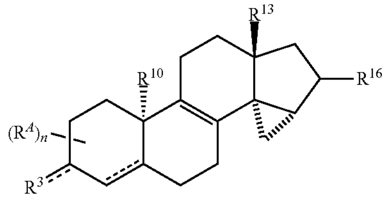

or (VII-D)

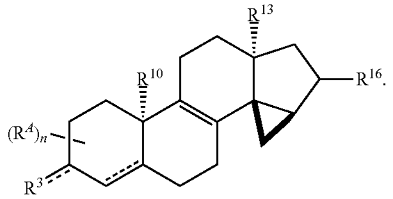

In certain embodiments, the compound has a structure corresponding to Formula (VII-A1), Formula (VII-B1), Formula (VII-C1), or Formula (VII-D1):

(VII-A1)

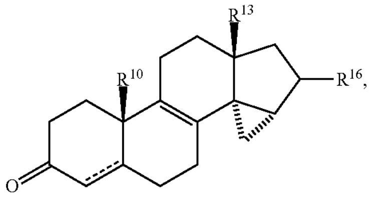

(VII-B1)

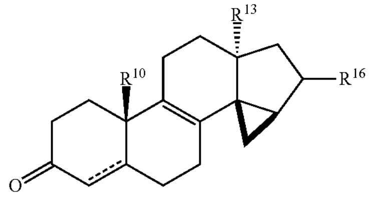

(VII-C1)

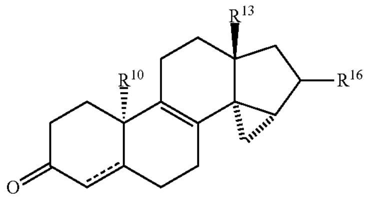

or (VII-D1)

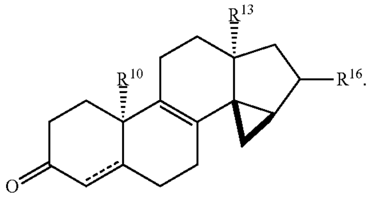

In certain embodiments, the compounds of Formula (VII-A), Formula (VII-B), Formula (VII-C), and Formula (VII-D) comprise a double bond between carbon C4 and carbon C5. In some such embodiments, $R^{16}$ represents a hydroxy group or a $C_{1-6}$-alkoxy group.

In certain embodiments, the compounds of Formula (VII-A), Formula (VII-B), Formula (VII-C), and Formula (VII-D) comprise a single bond between carbon C4 and carbon C5. In some such embodiments, $R^{16}$ represents a hydroxy group or a $C_{1-6}$-alkoxy group, In any aspect or embodiment described herein, a dashed or solid semi-circle (e.g., representing the A ring) represents a saturated or unsaturated carbocyclic or heterocyclic ring containing 5 or 6 ring atoms. In some such embodiments, the A ring is optionally substituted benzene. In other such embodiments, the A ring is an optionally substituted 6-membered carbocyclic ring that is saturated or partially unsaturated. In some such embodiments, the A ring is optionally substituted cyclohexene. In some such embodiments, the A ring is cyclohex-2-en-1-one. In some such embodiments, the A ring is optionally substituted cyclohexane. In some such embodiments, the A ring is cyclohexanone. In still other such embodiments, the A ring is a 5- or 6-membered heterocyclic ring, such as thiophene or furan.

In any aspect or embodiment described herein, variables shown in generic structures may have the following meanings:

m is an integer selected from the group consisting of 0, 1, 2, and 3;

n is an integer selected from the group consisting of 0, 1, 2, 3, 4, 5, 6, 7, and 8;

each $R^{A}$ is independently selected from the group consisting of hydrogen, $C_{1-10}$-alkyl, $C_{2-10}$-alkenyl, $C_{2-10}$-alkynyl, $C_{1-10}$-haloalkyl, halogen, oxo, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl, wherein $R^{AX}$ is hydrogen, $C_{1-6}$-alkyl, $C_{2-10}$-alkenyl, $C_{2-10}$-alkynyl, $C_{1-10}$-haloalkyl, —C(O)—$C_{1-10}$-alkyl, —C(O)—$C_{6-10}$-aryl, —C(O)-heteroaryl, —C(O)—O—$C_{1-10}$-alkyl, —C(O)—O—$C_{6-10}$-aryl, —C(O)—O-heteroaryl, —C(O)—$NR^{Z1}R^{Z2}$, —$S(O)_2NR^{Z1}R^{Z2}$, —$S(O)_2R^{Z1}$, $C_{6-10}$-aryl, or 5- to 10-membered heteroaryl, wherein $R^{AY}$ is hydrogen, $C_{1-6}$-alkyl, $C_{2-10}$-alkenyl, $C_{2-10}$-alkynyl, $C_{1-10}$-haloalkyl, —C(O)—$C_{1-10}$-alkyl, —C(O)—$C_{6-10}$-aryl, —C(O)-heteroaryl, $C_{6-10}$-aryl, or 5- to 10-membered heteroaryl, wherein each of $R^{Z1}$ and $R^{Z2}$ are independently hydrogen, $C_{1-6}$-alkyl, $C_{2-10}$-alkenyl, $C_{2-10}$-alkynyl, $C_{1-10}$-haloalkyl, —$(CH_2)_m$—$C_{6-10}$-aryl, —$(CH_2)_m$-5- to 10-membered heteroaryl, hydroxy, or $C_{1-6}$-alkoxy;

$R^3$ is oxo or —$OR^{3X}$, wherein $R^{3X}$ is hydrogen or $C_{1-6}$-alkyl;

each of $R^{6A}$ and $R^{6B}$ are independently absent or selected from the group consisting of hydrogen, $C_{1-10}$-alkyl, $C_{2-10}$-alkenyl, $C_{2-10}$-alkynyl, $C_{1-10}$-haloalkyl, and halogen;

each of $R^{7A}$ and $R^{7B}$ are independently selected from the group consisting of hydrogen, $C_{1-10}$-alkyl, $C_{2-10}$-alkenyl, $C_{2-10}$-alkynyl, $C_{1-10}$-haloalkyl, halogen, hydroxy, and oxo;

$R^9$ or $R^{10}$, when present, is A-$X^A$—$R^X$, wherein A is a $C_1$-$C_{14}$-alkylene, $C_1$-$C_{14}$-haloalkylene, $C_2$-$C_{14}$-alkenylene, $C_2$-$C_{14}$-haloalkenylene, $C_2$-$C_{14}$-alkynylene, $C_2$-$C_{14}$-haloalkynylene, each of which is optionally interrupted by one or more of —O—, —$NR^Z$—, —C(O)—, —C(O)O—, —OC(O)—, —C(O)$NR^Z$—, —$NR^Z$C(O)—, —$S(O)_y$—, —$S(O)_yNR^Z$—, —$NR^ZS(O)_y$—, —C(S)$NR^Z$—, —$NR^Z$C(S)—, $C_{6-10}$-aryl, or 5- to 10-membered heteroaryl;

$X^A$ is absent or selected from the group consisting of —O—, —$NR^Z$—, —C(O)—, —C(O)O—, —OC(O)—, —C(O)$NR^Z$—, —$NR^Z$C(O)—, —$S(O)_y$—, —$S(O)_yNR^Z$—, —$NR^ZS(O)_y$—, —C(S)$NR^Z$—, —$NR^Z$C(S)—, $C_{6-10}$-aryl, and 5- to 10-membered heteroaryl;

$R^X$ is selected from the group consisting of hydrogen, $C_{1-6}$-alkyl, $C_{1-6}$-haloalkyl, $C_{2-6}$-alkenyl, $C_{2-6}$-haloalkenyl, $C_{2-6}$-alkynyl, $C_{2-6}$-haloalkynyl, $C_{3-7}$-cycloalkyl, —C(O)—$C_{1-6}$-alkyl, —C(O)—$C_{6-10}$-aryl, —C(O)-heteroaryl, —C(O)—$NR^{Z1}R^{Z2}$, —$S(O)_2NR^{Z1}R^{Z2}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl;

wherein $R^Z$ is hydrogen, $C_{1-6}$-alkyl, $C_{1-6}$-haloalkyl, $C_{2-6}$-alkenyl, $C_{2-6}$-haloalkenyl, $C_{2-6}$-alkynyl, $C_{2-6}$-haloalkynyl, $C_{3-7}$-cycloalkyl, $C_{6-10}$-aryl, or 5- to 10-membered heteroaryl and y is 0, 1, or 2;

$R^{13}$ is selected from the group consisting of $C_1$-$C_{14}$-alkyl, $C_1$-$C_{14}$-haloalkyl, $C_2$-$C_{14}$-alkenyl, $C_2$-$C_{14}$-haloalkenyl, $C_2$-$C_{14}$-alkynyl, $C_2$-$C_{14}$-haloalkynyl, each of which is optionally interrupted by one or more of —O—, —$NR^Z$—, —C(O)—, —C(O)O—, —OC(O)—, —C(O)$NR^Z$—, —$NR^Z$C(O)—, —$S(O)_y$—, —$S(O)_yNR^Z$—, —$NR^ZS(O)_y$—, —C(S)$NR^Z$—, —$NR^Z$C(S)—, —$(CH_2)_m$—$C_{6-10}$-aryl, and —$(CH_2)_m$-5- to 10-membered heteroaryl;

$R^{14}$ is absent or selected from the group consisting of hydrogen, $C_{1-10}$-alkyl, $C_{2-10}$-alkenyl, $C_{2-10}$-alkynyl, $C_{1-10}$-haloalkyl, and halogen or $R^{14}$ together with $R^{15A}$ or $R^{15B}$ and the carbon atoms to which they are attached (C14 and C15, respectively) forms a $C_3$-$C_7$-carbocycle or a 3- to 7-membered heterocycle and wherein the $C_3$-$C_7$-carbocycle or 3- to 7-membered heterocycle is optionally substituted with one or more halogen, hydroxy, $C_{1-6}$-alkyl, $C_{1-6}$-haloalkyl, or $C_{1-6}$-alkoxy;

each of $R^{15A}$ and $R^{15B}$ are independently absent or selected from the group consisting of hydrogen, $C_{1-10}$-alkyl, $C_{2-10}$-alkenyl, $C_{2-10}$-alkynyl, $C_{1-10}$-haloalkyl, and halogen;

$R^{16}$ is selected from the group consisting of oxo and —$OR^D$, wherein $R^D$ is selected from the group consisting of hydrogen, $C_{1-10}$-alkyl, $C_{1-10}$-haloalkyl, $C_{2-10}$-alkenyl, $C_{2-10}$-haloalkenyl, $C_{2-10}$-alkynyl, $C_{2-10}$-haloalkynyl, —$(CH_2)_m$—$C_{6-10}$-aryl, —$(CH_2)_m$-5- to 10-membered heteroaryl, —C(O)—$C_{1-10}$-alkyl, —C(O)—$C_{1-10}$-haloalkyl, —C(O)—$C_{2-10}$-alkenyl, —C(O)—$C_{2-10}$-haloalkenyl, —C(O)—$C_{2-10}$-alkynyl, —C(O)—$C_{2-10}$-haloalkynyl, —C(O)—$(CH_2)_m$—$C_{6-10}$-aryl, —C(O)—$(CH_2)_m$-5- to 10-membered heteroaryl;

each of $R_{17A}$ and $R_{17B}$ are independently selected from the group consisting of hydrogen, $C_{1-10}$-alkyl, $C_{2-10}$-alkenyl, $C_{2-10}$-alkynyl, $C_{1-10}$-haloalkyl, halogen, hydroxy, $C_{1-6}$-alkoxy, $C_{1-10}$-alkyl-C(O), —C(O)—$C_{1-10}$-alkyl, —C(O)—$C_{1-10}$-hydroxyalkyl, —C(O)—$C_{1-10}$-alkyl-$C_{6-10}$-aryl, —C(O)—$C_{1-10}$-alkyl-heteroaryl, —C(O)—$C_{6-10}$-aryl, —C(O)-heteroaryl, —O—C(O)—$C_{1-6}$-alkyl, $C_{6-10}$-aryl, and 5- to 10-membered heteroaryl, or $R^{17A}$ and $R^{17B}$ together form an oxo;

W, together with carbon atoms C14 and C15 to which it is attached, forms a $C_3$-$C_7$-carbocycle or a 3- to 7-membered heterocycle and wherein the $C_3$-$C_7$-carbocycle or 3- to 7-membered heterocycle is optionally substituted with one or more halogen, hydroxy, $C_{1-6}$-alkyl, $C_{1-6}$-haloalkyl, or $C_{1-6}$-alkoxy; and each ---- independently represents a single bond or a double bond, provided that the bonds between C4-C5 and C5-C6 are not both double bonds and that the bonds between C8-C14 and C14-C15 are not both double bonds;

wherein any $C_{6-10}$-aryl or 5- to 10-membered heteroaryl is optionally substituted with one or more halogen, hydroxy, $C_{1-6}$-alkyl, $C_{1-6}$-haloalkyl, or $C_{1-6}$-alkoxy.

In certain preferred embodiments, n is 1 or 2. In some such preferred embodiments, n is 1. In some such preferred embodiments, n is 2.

In certain preferred embodiments, m is 0 or 1. In some such preferred embodiments, m is 0. In some such preferred embodiments, m is 1.

In certain preferred embodiments, $R^A$ is —OH, —O—$C_{1-6}$-alkyl, or oxo. In some such preferred embodiments, $R^A$ is —OH or oxo.

In certain preferred embodiments, n is 2 and one $R^A$ is —OH or —O—$C_{1-6}$-alkyl and the other $R^A$ is $C_{1-10}$-alkyl, such as methyl, or —$OR^{AX}$ wherein $R^{AX}$ is $C_{1-6}$-alkyl, such as methyl.

In certain preferred embodiments, $R^3$ is —OH or oxo. In some such preferred embodiments, $R^3$ is oxo.

In certain preferred embodiments, the bond between C4-C5 is a double bond and the bond between C5-C6 is a single bond.

In certain preferred embodiments, the bond between C4-C5 is a double bond, the bond between C5-C6 is a single bond, and $R^3$ is —OH or oxo. In some such preferred embodiments, the bond between C4-C5 is a double bond, the bond between C5-C6 is a single bond, and $R^3$ is oxo.

In certain preferred embodiments, the bond between C5-C6 is a single bond and both $R^{6A}$ and $R^{6B}$ are hydrogen, $R^{6A}$ is hydrogen and $R^{6B}$ is $C_{1-10}$-alkyl, and $R^{6A}$ is hydrogen and $R^{6B}$ is $C_{1-10}$-haloalkyl. In some such preferred embodiments, both $R^{6A}$ and $R^{6B}$ are hydrogen.

In certain preferred embodiments, both $R^{7A}$ and $R^{7B}$ are hydrogen, $R^{7A}$ is hydrogen and $R^{7B}$ is $C_{1-10}$-alkyl, and $R^{7A}$ is hydrogen and $R^{7B}$ is $C_{1-10}$-haloalkyl. In some such preferred embodiments, both $R^{7A}$ and $R^{7B}$ are hydrogen.

In certain preferred embodiments, $R^9$ is selected from the group consisting of $C_{1-10}$-alkyl, $C_{2-10}$-alkenyl, $C_{2-10}$-alkynyl, $C_{1-10}$-haloalkyl, —$(CH_2)_m$—$C_{6-10}$-aryl, and —$(CH_2)_m$-5- to 10-membered heteroaryl. In some such preferred embodiments, $R^9$ is $C_{1-10}$-alkyl. For example, $R^9$ may be methyl.

In certain preferred embodiments, $R^{13}$ is selected from the group consisting of $C_{1-14}$-alkyl and $C_{1-14}$-haloalkyl, each of which is optionally interrupted by one or more of —O—, —$NR^Z$—, —C(O)—, —C(O)O—, —OC(O)—, —C(O)$NR^Z$—, —$NR^Z$C(O)—, —$S(O)_y$—, —$S(O)_yNR^Z$—, —$NR^ZS(O)_y$—, —C(S)$NR^Z$—, and —$NR^Z$C(S)—. In some such preferred embodiments, $R^{13}$ is $C_{1-14}$-alkyl. For example, $R^{13}$ may be methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl. In some embodiments, $R^{13}$ is a $C_4$-alkyl. In some embodiments, $R^{13}$ is a $C_5$-alkyl. In some embodiments, $R_{13}$ is a $C_6$-alkyl. In some embodiments, $R^{13}$ is a $C_7$-alkyl. In some embodiments, $R^{13}$ is a $C_8$-alkyl. In some embodiments, $R^{13}$ is a $C_9$-alkyl. In some embodiments, $R^{13}$ is a $C_{10}$-alkyl. In some embodiments, $R^{13}$ is a $C_{11}$-alkyl. In some embodiments, $R^{13}$ is a $C_{12}$-alkyl. In some embodiments, $R^{13}$ is a $C_{13}$-alkyl. In some embodiments, $R^{13}$ is a $C_{14}$-alkyl.

In certain preferred embodiments, the bond between C8-C14 is a double bond and the bond between C14-C15 is a single bond.

In certain preferred embodiments, the bond between C14-C15 is a single bond and both $R^{15A}$ and $R^{15B}$ are hydrogen, $R^{15A}$ is hydrogen and $R^{15B}$ is $C_{1-10}$-alkyl, and $R^{15A}$ is hydrogen and $R^{15B}$ is $C_{1-10}$-haloalkyl. In some such preferred embodiments, both $R^{15A}$ and $R^{15B}$ are hydrogen.

In certain preferred embodiments, $R^{16}$ is —OH, —O—$C_{1-6}$-alkyl, or —O—C(O)—$C_{1-10}$-alkyl. In some such preferred embodiments, $R^{16}$ is —OH or —O—C(O)—$C_{1-10}$-alkyl. In certain preferred embodiments, $R^{16}$ is —$OR^D$ and $R^D$ is selected from the group consisting of hydrogen, $C_{1-10}$-alkyl, $C_{1-10}$-haloalkyl, $C_{2-10}$-alkenyl, $C_{2-10}$-haloalkenyl, $C_{2-10}$-alkynyl, $C_{2-10}$-haloalkynyl, —$(CH_2)_m$—$C_{6-10}$-aryl, and —$(CH_2)_m$-5- to 10-membered heteroaryl. In some such embodiments, $R^D$ is hydrogen, $C_{1-6}$-alkyl, or $C_{1-6}$-haloalkyl. In certain preferred embodiments, $R^{16}$ is —O—C(O)$R^D$ and $R^D$ is selected from the group consisting of hydrogen, $C_{1-6}$-alkyl, $C_{1-6}$-haloalkyl, $C_{2-6}$-alkenyl, $C_{2-6}$-haloalkenyl, $C_{2-6}$-alkynyl, $C_{2-6}$-haloalkynyl, —$(CH_2)_m$—$C_{6-10}$-aryl, and —$(CH_2)_m$-5- to 10-membered heteroaryl. In some such embodiments, $R^D$ is hydrogen, $C_{1-6}$-alkyl, or $C_{1-6}$-haloalkyl.

In certain preferred embodiments, both $R^{17A}$ and $R^{17B}$ are hydrogen, $R^{17A}$ is hydrogen and $R^{17B}$ is $C_{1-10}$-alkyl, and $R^{17A}$ is hydrogen and $R^{17B}$ is $C_{1-10}$-haloalkyl. In some such preferred embodiments, both $R^{17A}$ and $R^{17B}$ are hydrogen. In certain preferred embodiments, neither $R^{17A}$ nor $R^{17B}$ are hydroxy.

It is to be understood that any preferred embodiment for a variable (e.g., n, $R^A$, $R^{6A}$, $R^{6B}$, $R^{7A}$, $R^{7B}$, $R^9$, $R^{13}$, $R^{15A}$, $R^{15B}$, $R^{16}$, $R^{17A}$, and $R^{17B}$) may be combined with any preferred embodiment for any other variable(s) described herein. Exemplary combinations for compounds having a structure corresponding to formulae described herein include, but are not limited to: n is 0 or 1; $R^A$, if present, is hydroxy or oxo; $R^3$ is hydroxy or oxo; the bond between C4-C5 is a double bond and the bond between C5-C6 is a single bond; $R^{6A}$ and $R^{6B}$ are both hydrogen; $R^{7A}$ and $R^{7B}$ are both hydrogen; $R^9$ is $C_{1-6}$-alkyl; $R^{13}$ is $C_{1-10}$-alkyl; the bond between C8-C14 is a double bond and the bond between C14-C15 is a single bond; $R^{15A}$ and $R^{15B}$ are both hydrogen; $R^{16}$ is —OH or —O—C(O)—$C_{1-8}$-alkyl; and $R^{17A}$ and $R^{17B}$ are both hydrogen.

In one aspect, this disclosure provides a compound or salt or prodrug thereof, wherein the compound has a structure corresponding to one of the listed in Table A.

Data for select compounds are shown in Table A:

| Ex. | Structure | $IC_{50}$ (nM) | Ki (nM) |
|---|---|---|---|
| 101 | 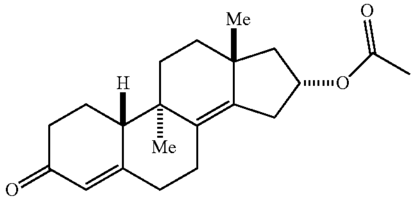<br>Chemical Formula: $C_{21}H_{28}O_3$<br>Exact Mass: 328.20<br>Molecular Weight: 328.45<br>m/z: 328.20 (100.0%), 329.21 (23.1%), 330.21 (3.2%)<br>Elemental Analysis: C, 76.79; H, 8.59; O, 14.61 | 413 | 7350 |
| 102 | 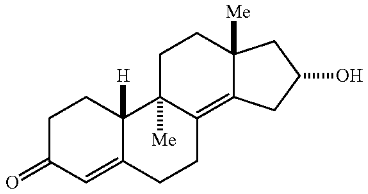<br>Chemical Formula: $C_{19}H_{26}O_2$<br>Exact Mass: 286.19<br>Molecular Weight: 286.42<br>m/z: 286.19 (100.0%), 287.20 (20.9%), 288.20 (2.5%)<br>Elemental Analysis: C, 79.68; H, 9.15; O, 11.17 | 654 | 919 |
| 103 | 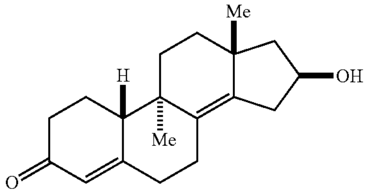<br>Chemical Formula: $C_{19}H_{26}O_2$<br>Exact Mass: 286.19<br>Molecular Weight: 286.42<br>m/z: 286.19 (100.0%), 287.20 (20.9%), 288.20 (2.5%)<br>Elemental Analysis: C, 79.68; H, 9.15; O, 11.17 | 1243 | 3457 |
| 104 | 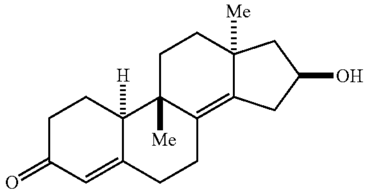<br>Chemical Formula: $C_{19}H_{26}O_2$<br>Exact Mass: 286.19<br>Molecular Weight: 286.42<br>m/z: 286.19 (100.0%), 287.20 (20.9%), 288.20 (2.5%)<br>Elemental Analysis: C, 79.68; H, 9.15; O, 11.17 | 4300 | |
| 105 | 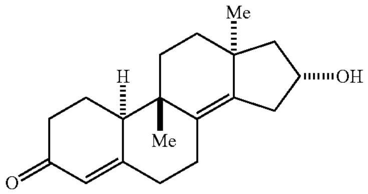<br>Chemical Formula: $C_{19}H_{26}O_2$<br>Exact Mass: 286.1933<br>Molecular Weight: 286.4150<br>m/z: 286.1933 (100.0%), 287.1966 (20.5%), 288.2000 (2.0%)<br>Elemental Analysis: C, 79.68; H, 9.15; O, 11.17 | 1500 | |

-continued

| Ex. | Structure | $IC_{50}$ (nM) | Ki (nM) |
|---|---|---|---|
| 106 | 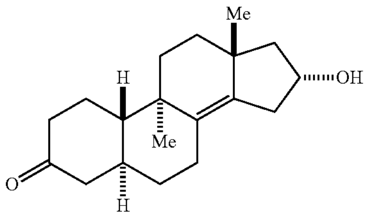 Chemical Formula: $C_{19}H_{28}O_2$ Exact Mass: 288.21 Molecular Weight: 288.43 m/z: 288.21 (100.0%), 289.21 (20.6%), 290.22 (2.1%) Elemental Analysis: C, 79.12; H, 9.79; O, 11.09 | 1800 | |
| 107 | 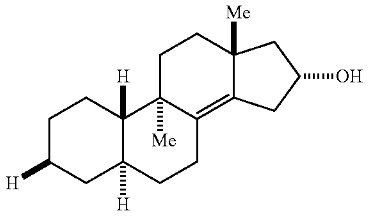 Chemical Formula: $C_{19}H_{30}O_2$ Exact Mass: 290.22 Molecular Weight: 290.45 m/z: 290.22 (100.0%), 291.23 (21.0%), 292.23 (2.5%) Elemental Analysis: C, 78.57; H, 10.41; O, 11.02 | 4800 | |
| 108 | 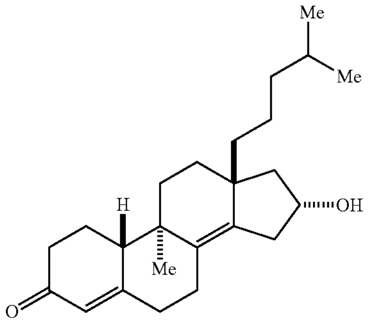 Chemical Formula: $C_{24}H_{36}O_2$ Exact Mass: 356.27 Molecular Weight: 356.55 m/z: 356.27 (100.0%), 357.27 (26.0%), 358.28 (3.8%) Elemental Analysis: C, 80.85; H, 10.18; O, 8.97 | 84 | 236 |
| 109 | 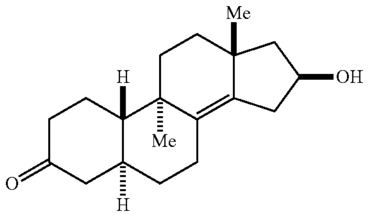 Chemical Formula: $C_{19}H_{28}O_2$ Exact Mass: 288.21 Molecular Weight: 288.43 m/z: 288.21 (100.0%), 289.21 (20.6%), 290.22 (2.1%) Elemental Analysis: C, 79.12; H, 9.79; O, 11.09 | 6800 | |

-continued

| Ex. | Structure | $IC_{50}$ (nM) | Ki (nM) |
|---|---|---|---|
| 110 | 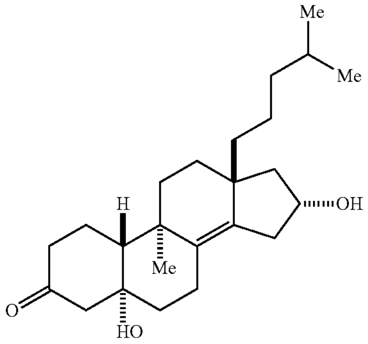 Chemical Formula: $C_{24}H_{38}O_2$ Exact Mass: 358.29 Molecular Weight: 358.57 m/z: 358.29 (100.0%), 359.29 (26.5%), 360.29 (3.7%) Elemental Analysis: C, 80.39; H, 10.68; O, 8.92 | 696 | 1704 |
| 201 | 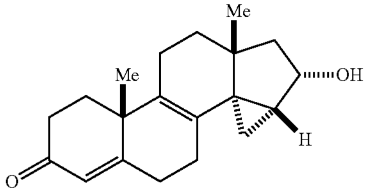 Chemical Formula: $C_{20}H_{26}O_2$ Exact Mass: 298.19 Molecular Weight: 298.43 m/z: 298.19 (100.0%), 299.20 (22.0%), 300.20 (2.7%) Elemental Analysis: C, 80.50; H, 8.78; O, 10.72 | 218 | 1400 |
| 202 | 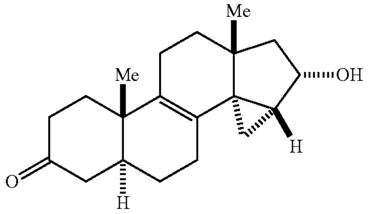 Chemical Formula: $C_{20}H_{28}O_2$ Exact Mass: 300.21 Molecular Weight: 300.44 m/z: 300.21 (100.0%), 301.21 (21.7%), 302.22 (2.3%) Elemental Analysis: C, 79.96; H, 9.39; O, 10.65 | 61 | 837 |
| 203 | 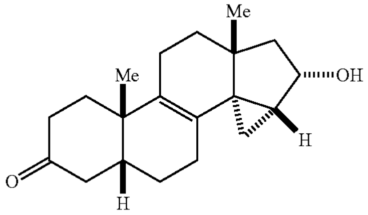 Chemical Formula: $C_{20}H_{28}O_2$ Exact Mass: 300.21 Molecular Weight: 300.44 m/z: 300.21 (100.0%), 301.21 (21.7%), 302.22 (2.3%) Elemental Analysis: C, 79.96; H, 9.39; O, 10.65 | 1180 | |

-continued
| Ex. | Structure | $IC_{50}$ (nM) | Ki (nM) |
|---|---|---|---|
| 204 | 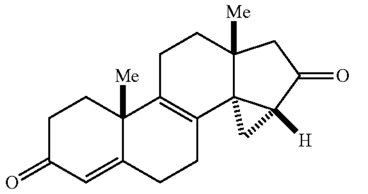 Chemical Formula: $C_{20}H_{24}O_2$ Exact Mass: 296.18 Molecular Weight: 296.41 m/z: 296.18 (100.0%), 297.18 (22.0%), 298.18 (2.6%) Elemental Analysis: C, 81.04; H, 8.16; O, 10.80 | | |
| 205 | 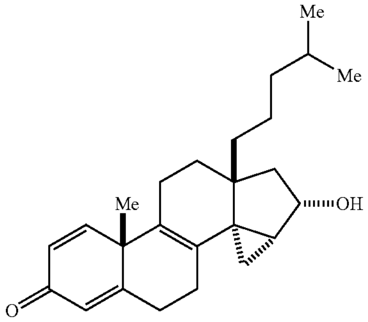 Chemical Formula: $C_{25}H_{34}O_2$ Exact Mass: 366.26 Molecular Weight: 366.55 m/z: 366.26 (100.0%), 367.26 (27.5%), 368.26 (3.9%) Elemental Analysis: C, 81.92; H, 9.35; O, 8.73 | | |
| 206 | 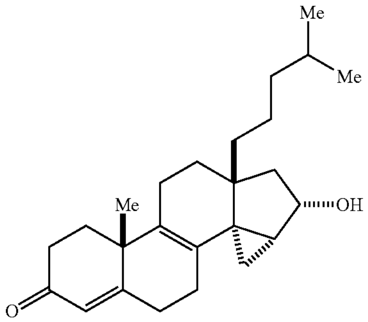 Chemical Formula: $C_{25}H_{36}O_2$ Exact Mass: 368.27 Molecular Weight: 368.56 m/z: 368.27 (100.0%), 369.27 (27.0%), 370.28 (4.1%) Elemental Analysis: C, 81.47; H, 9.85; O, 8.68 | | |

-continued

| Ex. | Structure | $IC_{50}$ (nM) | Ki (nM) |
|---|---|---|---|
| 207 | 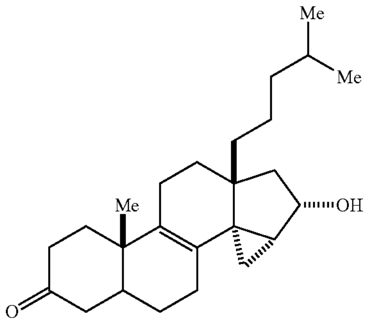<br>Chemical Formula: $C_{25}H_{38}O_2$<br>Exact Mass: 370.29<br>Molecular Weight: 370.58<br>m/z: 370.29 (100.0%), 371.29 (27.6%), 372.29 (3.9%)<br>Elemental Analysis: C, 81.03; H, 10.34; O, 8.63 | | |
| 208 | 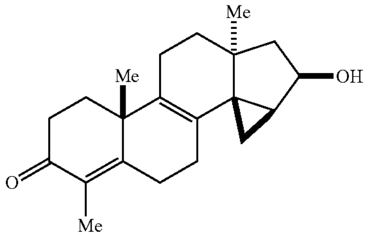<br>Chemical Formula: $C_{21}H_{28}O_2$<br>Exact Mass: 312.21<br>Molecular Weight: 312.45<br>m/z: 312.21 (100.0%), 313.21 (22.8%), 314.22 (2.5%)<br>Elemental Analysis: C, 80.73; H, 9.03; O, 10.24 | | |
| | enzalutamide | 63 | 2723 |

C. Synthetic Methods

The following general scheme is representative of a particular embodiment of the method and allows for concise and stereoselective synthesis of "C19" tetracyclic compounds:

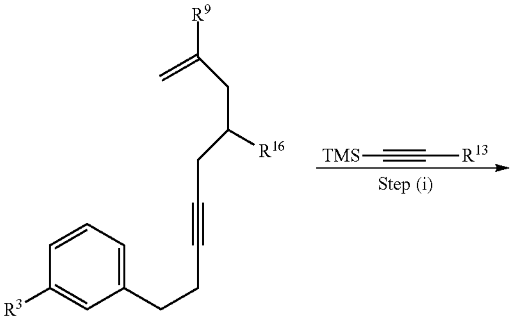

Enyne (a)

-continued

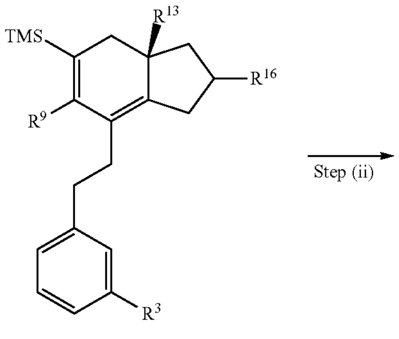

Hydrindane (a)

-continued

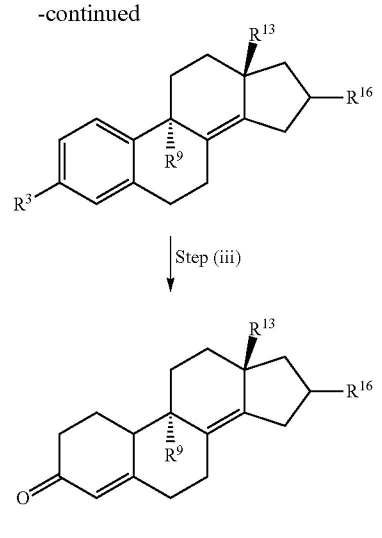

Step (i) is a metallacycle-mediated annulation reaction between readily available Enyne (a) and an optionally substituted alkyne (e.g., in the presence of $Ti(Oi\text{-}Pr)_4$, n-BuLi, and PhMe) to provide Hydrindane (a), which possesses the C13 quaternary center. While step (i) depicts an optionally substituted trimethylsilypropyne, alternative compounds such as those having a simple internal alkyne (without a TMS) or an alternative to the silyl group (or stannyl group, for example) on the alkyne may also be used.

Step (ii) is a cyclization reaction through C9-C10 bond-formation, such as by an intramolecular regio- and stereo-selective Friedel-Crafts cyclization of stereoselective Heck cyclization (for example, where the A ring of Hydrindane (a) further comprises a group suitable for an intramolecular Heck reaction such as halogen or —OTf).

In one aspect, the present disclosure provides a method for shifting a substituent of a steroidal tetracycle from C9 to C10. The following general scheme is representative of a particular embodiment of the method:

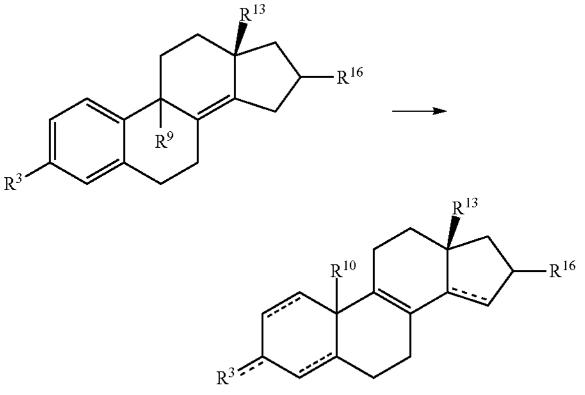

In certain embodiments, an oxidative rearrangement marked by a 1,2-alkyl shift from C9 to C10 is employed. In some such embodiments, concomitant establishment of an A-ring dienone is achieved.

In certain embodiments, the method is carried out in the presence of an oxidant. In certain embodiments, the oxidant is an aryliodine(III) carboxylate, such as is phenyliodo(III) diacetate (PIDA) or (bis(trifluoroacetate)iodo)benzene (PIFA). In some such embodiments, the oxidant is phenyliodo(III)diacetate (PIDA).

D. Methods of Use

In at least one aspect, the present disclosure includes a method for inhibiting androgen receptor activity. The method comprises exposing an androgen receptor to and/or contacting an androgen receptor with an effective amount of a compound described herein (including, but not limited to, Compounds 101-110 and Compounds 201-207) or a pharmaceutically acceptable salt or prodrug thereof.

In at least one aspect, the present disclosure includes a method for treating or preventing an androgen-dependent condition in a subject in need of such treatment or prevention. In certain embodiments, the androgen-dependent condition is a proliferative disease. Exemplary proliferative diseases include cancers (i.e., "malignant neoplasms") and benign neoplasms. In particular, exemplary proliferative diseases that may be treated or prevented include prostate cancer and benign prostatic hyperplasia ("BPH"). In certain embodiments, the androgen-dependent condition is cancer (e.g., prostate cancer), BPH, hypersexuality, acne, amenorrhea, seborrhea, hirsutism, androgenic alopecia, hidradenitis suppurativa, or hyperandrogenism.

Thus, one aspect of the present disclosure includes a method for treating prostate cancer. The method comprises administering to a patient in need thereof a therapeutically effective amount of a compound described herein (including, but not limited to, Compounds 101-110 and Compounds 201-202) or a pharmaceutically acceptable salt or prodrug thereof. In some embodiments, the compound is a compound listed in Table A. In some embodiments, the compound is Compound 108. In some embodiments, the compound is Compound 201. In some embodiments, the compound is Compound 202. In some embodiments, the compound (or pharmaceutically acceptable salt thereof) is administered orally. In some embodiments, the compound (or pharmaceutically acceptable salt thereof) is administered parenterally, such as intramuscularly, subcutaneously, or transdermally. In at least one aspect, the present disclosure includes a compound disclosed herein or a pharmaceutically acceptable salt or prodrug thereof for use in a method for treating a cancer, particularly prostate cancer. In certain embodiments, the compound is a compound listed in Table A. In certain embodiments, a compound described herein (including, but not limited to, Compounds 101-110 and Compounds 201-207) or a pharmaceutically acceptable salt or prodrug thereof can be used in combination with one or more additional therapeutic agents. In certain embodiments, the prostate cancer is castration-resistant prostate cancer ("CRPC"), particularly metastatic CRPC.

Another aspect of the present disclosure includes a method for treating or preventing BPH in a subject in need of such treatment or prevention.

Still another aspect of the present disclosure includes a method for treating or preventing hypersexuality, acne, amenorrhea, seborrhea, hirsutism, androgenic alopecia, hidradenitis suppurativa, or hyperandrogenism in a subject in need of such treatment or prevention.

One aspect of the present disclosure includes a method for treating or preventing a disease or condition that is at least partially mediated or affected by an androgen receptor (AR) in a subject in need of such treatment or prevention.

Another aspect of the present disclosure includes a method for treating or preventing a disease or condition treatable or preventable by selectively modulating AR in a subject in need of such treatment or prevention.

In certain embodiments, for any of the aforementioned aspects, the subject is a mammal. In some such embodiments, the mammal is a human.

In certain embodiments, for any of the aforementioned aspects, the methods comprise administering to the subject a therapeutically effective amount of a compound described herein (including, but not limited to, Compounds 101-110 and Compounds 201-207) or a pharmaceutically acceptable salt or prodrug thereof as single agent or in combination with another therapeutic agent. In some such embodiments, the methods comprise administering to the subject a therapeutically effective amount of one of Compound 101-110 or a pharmaceutically acceptable salt or prodrug thereof, preferably one of Compound 101-110. In some such embodiments, the methods comprise administering to the subject a therapeutically effective amount of one of Compound 201-202 or a pharmaceutically acceptable salt or prodrug thereof, preferably one of Compound 201-202. For example, in one particular embodiment, the method comprises administering to the subject a therapeutically effective amount of Compound 108 or a pharmaceutically acceptable salt or prodrug thereof, preferably Compound 108. In another particular embodiment, the method comprises administering to the subject a therapeutically effective amount of Compound 202 or a pharmaceutically acceptable salt or prodrug thereof, preferably Compound 202. In certain embodiments, the compound is administered orally.

In some such embodiments, the compound has a structure corresponding to Formula (III-A1.1), (III-A1.2), (III-A1.3), (III-B1.1), (III-B1.2), or (III-B1.3):

(III-A1.1)

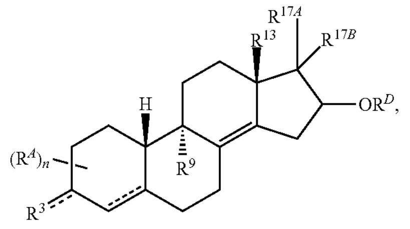

(III-B1.1)

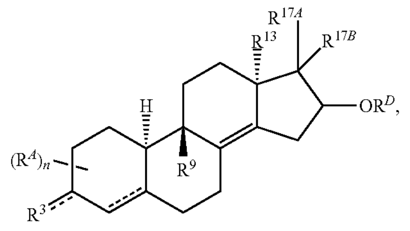

(III-A1.2)

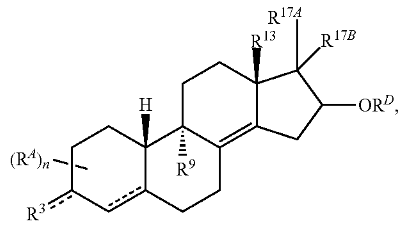

-continued (III-B1.2)

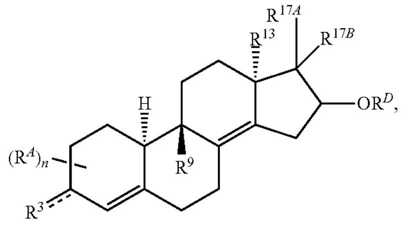

(III-A1.3)

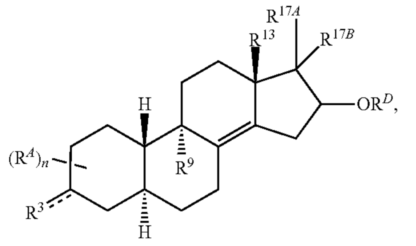

or (III-B1.3)

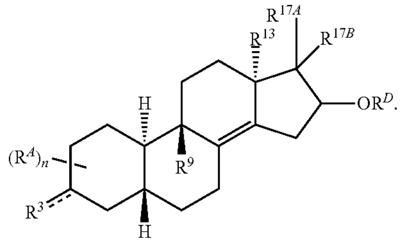

In certain preferred embodiments, n is 0, 1, or 2. In some such preferred embodiments, n is 0.

In certain preferred embodiments, $R^A$ is $C_{1-10}$-alkyl, such as methyl,

In certain preferred embodiments, $R^3$ is oxo or —OH.

In certain preferred embodiments, $R^9$ is an aliphatic group that projects an electron density beyond the traditional bounds of the androgen receptor ligand binding pocket. In some such preferred embodiments, $R^9$ is $C_{1-10}$-alkyl, $C_{1-10}$-haloalkyl, or $—(CH_2)_m—C_{6-10}$-aryl. In some such preferred embodiments, $R^9$ is $C_{1-10}$-alkyl, such as methyl, ethyl, or propyl. In some such preferred embodiments, $R^9$ is $—(CH_2)_m—C_{6-10}$-aryl, wherein m is 0 or 1. For example, $R^{10}$ may be phenyl or benzyl.

In certain preferred embodiments, $R^{13}$ is $C_{1-10}$-alkyl, $C_{1-10}$-haloalkyl, or $—(CH_2)_m—C_{6-10}$-aryl. In some such preferred embodiments, $R^{13}$ is $C_{1-10}$-alkyl, such as methyl, ethyl, propyl, butyl (e.g., n-butyl or isobutyl), pentyl, or hexyl (e.g., n-hexyl or methylpentyl). In some such preferred embodiments, $R^{13}$ is $—(CH_2)_m—C_{6-10}$-aryl, wherein m is 0 or 1. For example, $R^{13}$ may be phenyl or benzyl.

In certain preferred embodiments, $R^{17A}$ and $R^{17B}$ are both hydrogen.

In certain preferred embodiments, $R^D$ is hydrogen or $—C(O)—C_{1-10}$-alkyl. In some such preferred embodiments, $R^D$ is hydrogen. In some such preferred embodiments, $R^D$ is $—C(O)—C_{1-6}$-alkyl.

In some such embodiments, the compound has a structure corresponding to Formula (VII-A1), (VII-B1), (VII-C1), or (VII-D1):

(VII-A1)

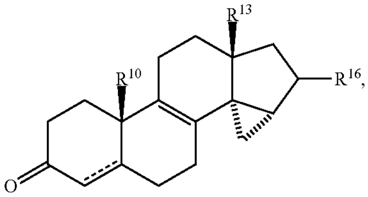

(VII-B1)

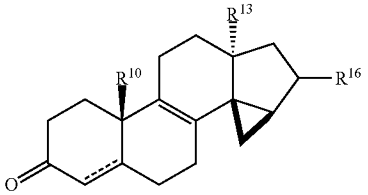

(VII-C1)

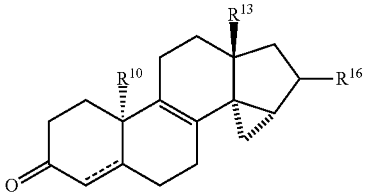

or (VII-D1)

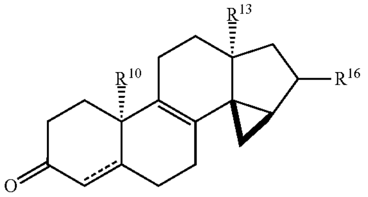

In certain preferred embodiments, the bond between carbon C4 and carbon C5 is a double bond.

In certain preferred embodiments, $R^{10}$ is $C_{1-10}$-alkyl, $C_{1-10}$-haloalkyl, or $-(CH_2)_m-C_{6-10}$-aryl. In some such preferred embodiments, $R^{10}$ is $C_{1-10}$-alkyl, such as methyl, ethyl, or propyl. In some such preferred embodiments, $R^{10}$ is $-(CH_2)_m-C_{6-10}$-aryl, wherein m is 0 or 1. For example, $R^{10}$ may be phenyl or benzyl.

In certain preferred embodiments, $R^{13}$ is $C_{1-10}$-alkyl, $C_{1-10}$-haloalkyl, or $-(CH_2)_m-C_{6-10}$-aryl. In some such preferred embodiments, $R^{13}$ is $C_{1-10}$-alkyl, such as methyl, ethyl, propyl, butyl (e.g., n-butyl or isobutyl), pentyl, or hexyl (e.g., n-hexyl or methylpentyl). In some such preferred embodiments, $R^{13}$ is $-(CH_2)_m-C_{6-10}$-aryl, wherein m is 0 or 1. For example, $R^{13}$ may be phenyl or benzyl.

In certain preferred embodiments, $R^{16}$ is $-OR^D$ and $R^D$ is hydrogen or $-C(O)-C_{1-10}$-alkyl. In some such preferred embodiments, $R^D$ is hydrogen. In some such preferred embodiments, $R^D$ is $-C(O)-C_{1-6}$-alkyl. In some such embodiments, $R^{16}$ is in the alpha orientation.

The preferred total daily dose of the compound or salt (administered in single or divided doses) is typically from about 0.001 to about 100 mg/kg, more preferably from about 0.001 to about 30 mg/kg, and even more preferably from about 0.01 to about 10 mg/kg (i.e., mg of the compound or salt per kg body weight). In certain embodiments, dosage unit compositions contain such amounts or submultiples thereof to make up the daily dose. In many instances, the administration of the compound or salt will be repeated a plurality of times. In certain embodiments, multiple doses per day typically may be used to increase the total daily dose, if desired.

Factors affecting the preferred dosage regimen include the type, age, weight, sex, diet, and condition of the patient; the severity of the pathological condition; the route of administration; pharmacological considerations, such as the activity, efficacy, pharmacokinetic, and toxicology profiles of the particular compound or salt used; whether a drug delivery system is utilized; and whether the compound or salt is administered as part of a drug combination. Thus, the dosage regimen actually employed can vary widely, and therefore, can derive from the preferred dosage regimen set forth above.

The activity of a compound can be determined using various known methods. For example, AR assays can be used. Such AR assays include binding assays using, for example, cells transfected with the human androgen receptor. Several cell based model systems that allow sensitive detection and monitoring of steroids or other compounds with AR bioactivity are known. Most cell based AR reporter models use transgenic gene constructs that include an androgen response element (ARE) that controls reporter gene (e.g., lucifersrase) expression. For example, a human AR Reporter Assay System is commercially available from Indigo Biosciecnes. The principle application of such an assay product is to quantify functional activities, either agonist or antagonist, that a compound may exert against the human androgen receptor. An exemplary assay system or test kit includes reporter cells, a reference agonist (e.g., 6α-fluoro-testosterone), and a reference antagonist (e.g., bicalutamide or hydroxyflutamide). In addition, the antiproliferative activity of a compound can be determined using various known methods, including in vitro and in vivo antiproliferative assays using cancer cell lines such as a prostate cancer cell line.

E. Compositions

In at least one aspect, the present disclosure includes compositions comprising a compound described herein (including, but not limited to, Compounds 101-110 and Compounds 201-202) or a pharmaceutically acceptable salt or prodrug thereof. In certain embodiments, the composition comprises one or more conventional pharmaceutically acceptable excipients.

In at least one aspect, the present disclosure includes compositions comprising an enantiomeric compound described herein. In certain embodiments, the composition is enantiomerically pure or enriched. For example, the composition may comprise at least 85% of one enantiomer and not more than 15% of the other enantiomer; alternatively, at least 90% of one enantiomer and not more than 10% of the other enantiomer; alternatively, at least 95% of one enantiomer and not more than 5% of the other enantiomer; alternatively, at least 97% of one enantiomer and not more than 3% of the other enantiomer; or alternatively, at least 99% of one enantiomer and not more than 1% of the other enantiomer. In certain embodiments, the composition is substantially free of enantiomeric impurities. In some such embodiments, the composition is free of any detectable amount of an enantiomeric impurity.

Pharmaceutical compositions disclosed herein comprise a compound disclosed herein or a pharmaceutically acceptable salt or prodrug thereof, preferably, Compounds 101-110 or Compounds 201-202. In some embodiments, the pharmaceutical composition is an oral dosage form, preferably a solid oral dosage form (e.g., a tablet). In some such embodiments, the solid oral dosage form may comprise pharmaceutically acceptable excipients such as excipients that function as binders, glidants, lubricants, and fillers. Thus, a solid oral dosage form comprising a compound disclosed herein or a pharmaceutically acceptable salt thereof further optionally comprises one or more conventional pharmaceutically acceptable excipients.

In some embodiments, a compound is co-administered with at least one additional therapeutic agent. In some such embodiments, the additional therapeutic agent is a corticosteroid, such as prednisone or prednisolone. In some such embodiments, the additional therapeutic agent is an estrogen, such as estradiol, ethinyl estradiol, or a conjugated estrogen. In some such embodiments, the additional therapeutic agent is a CYP17A1 inhibitor, such as abiraterone acetate or galeterone. In some such embodiments, the additional therapeutic agent is a nonsteroidal antiandrogen (NSAA) medication, such as flutamide, nilutamide, bicalutamide, topilutamide, apalutamide, enzalutamide, darolutamide, proxalutamide, or seviteronel.

In some embodiments, the additional therapeutic agent and the compound of the present disclosure are co-administered to the patient in a substantially simultaneous manner (e.g., or within about 5 min of each other), in a sequential manner, or both. It is contemplated, for example, that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. In some embodiments, the additional therapeutic agent and the compound of the present disclosure are administered in separate pharmaceutical compositions. In some embodiments, the additional therapeutic agent and the compound of the present disclosure are administered in the same pharmaceutical composition.

In at least one aspect, the present disclosure includes a pharmaceutical composition for treating an androgen-dependent condition such as prostate cancer or BPH, the composition comprising a compound disclosed herein or a pharmaceutically acceptable salt thereof and a pharmaceutically acceptable excipient. In certain embodiments, the compound is one of Compounds 101-110.

It will be readily apparent to those skilled in the art that other suitable modifications and adaptations of the compositions and methods of the invention described herein may be made using suitable equivalents without departing from the scope of the invention or the embodiments disclosed herein.

The compounds, compositions, and methods described herein will be better understood by reference to the following examples, which are included as an illustration of and not a limitation upon the scope of the invention.

F. Examples

Example 1

Compound 101—(9R,10S,13R,16S)-9,13-dimethyl-3-oxo-2,3,6,7,9,10,11,12,13,15,16,17-dodecahydro-1H-cyclopenta[a]phenanthren-16-yl acetate Compound 102—(9R,10S,13R,16S)-16-hydroxy-9,13-dimethyl-1,2,6,7,9,10,11,12,13,15,16,17-dodecahydro-3H-cyclopenta[a]phenanthren-3-one Compound 103—(9R,10S,13R,16R)-16-hydroxy-9,13-dimethyl-1,2,6,7,9,10,11,12,13,15,16,17-dodecahydro-3H-cyclopenta[a]phenanthren-3-one Compound 102 was prepared in 3 steps from Enyne 1, which is available from, for example, epichlorohydrin.

Preparation of Compound 102 from Enyne 1:

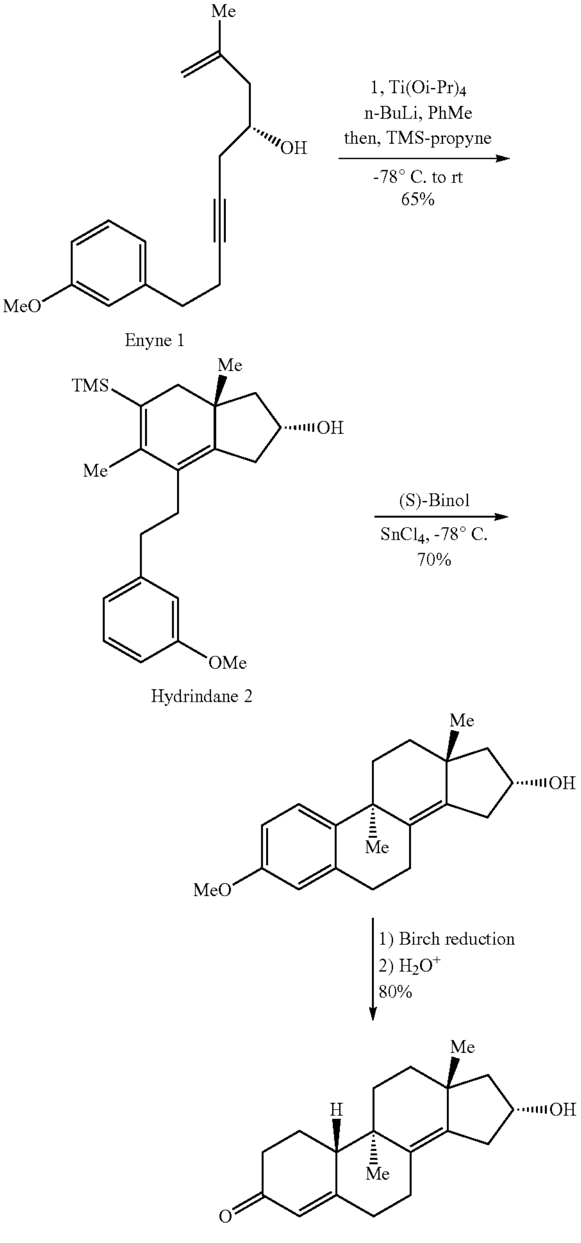

Enyne 1

Hydrindane 2

Compound 102

The first step was a titanium-mediated annulation reaction as generally described above to provide the stereodefined Hydrindane 2.

In the second step, Hydrindane 2, which is a silyl-substituted diene, was reacted with (S)-Binol and $SnCl_4$ at −78° C. to deliver the intermediate tetracyclic steroid product.

In the third step, the aromatic A ring was converted to a cyclohexanone to provide Compound 102.

Compounds 101 and 103-110 were prepared in a similar manner.

Figure 4:
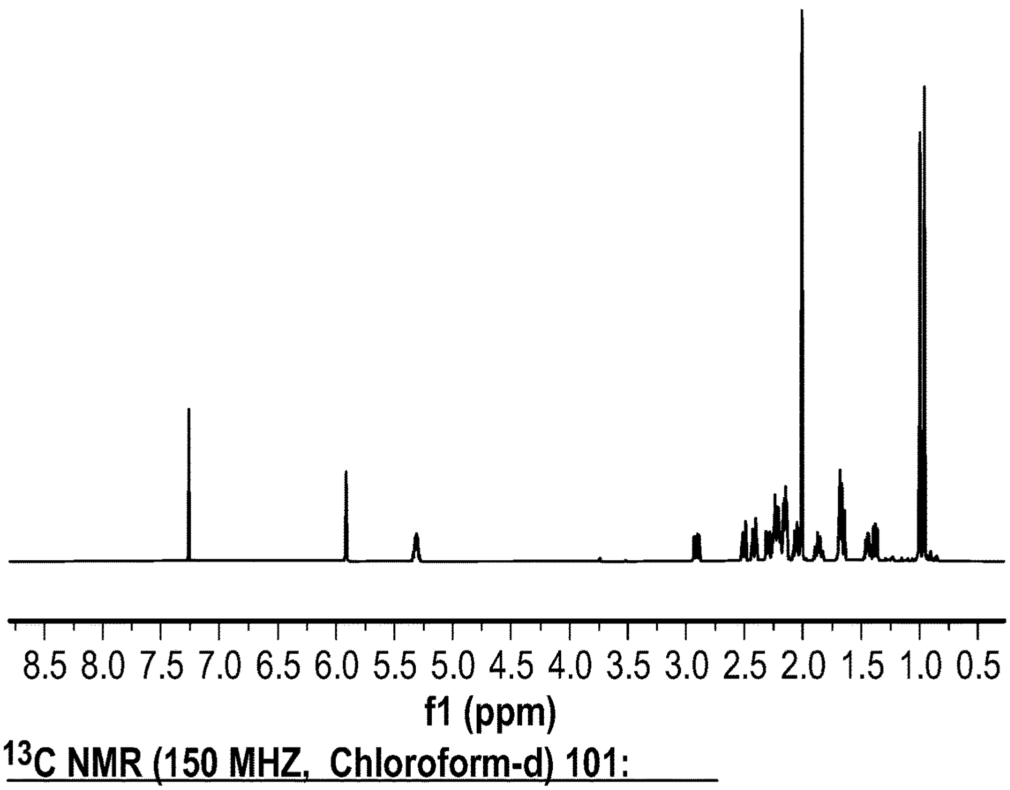
FIG. 4 shows $^{1}H$ NMR and $^{13}C$ NMR spectra for Compounds 101-110.
Figure 4:
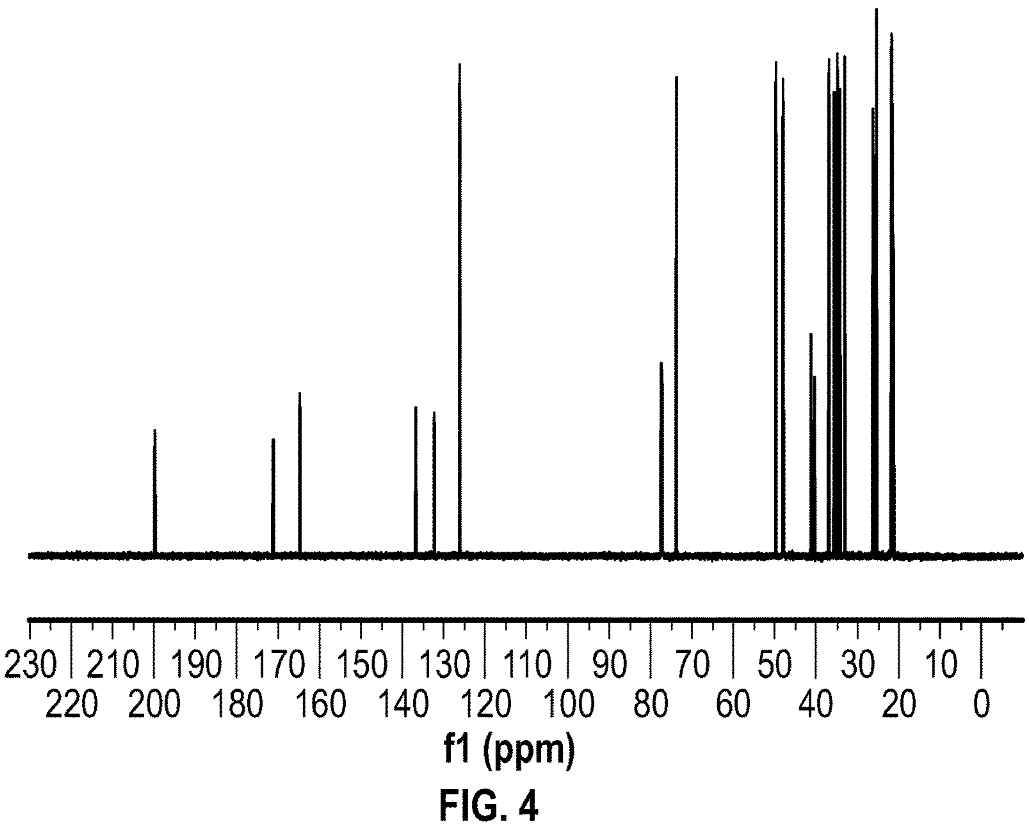
Figure 4:
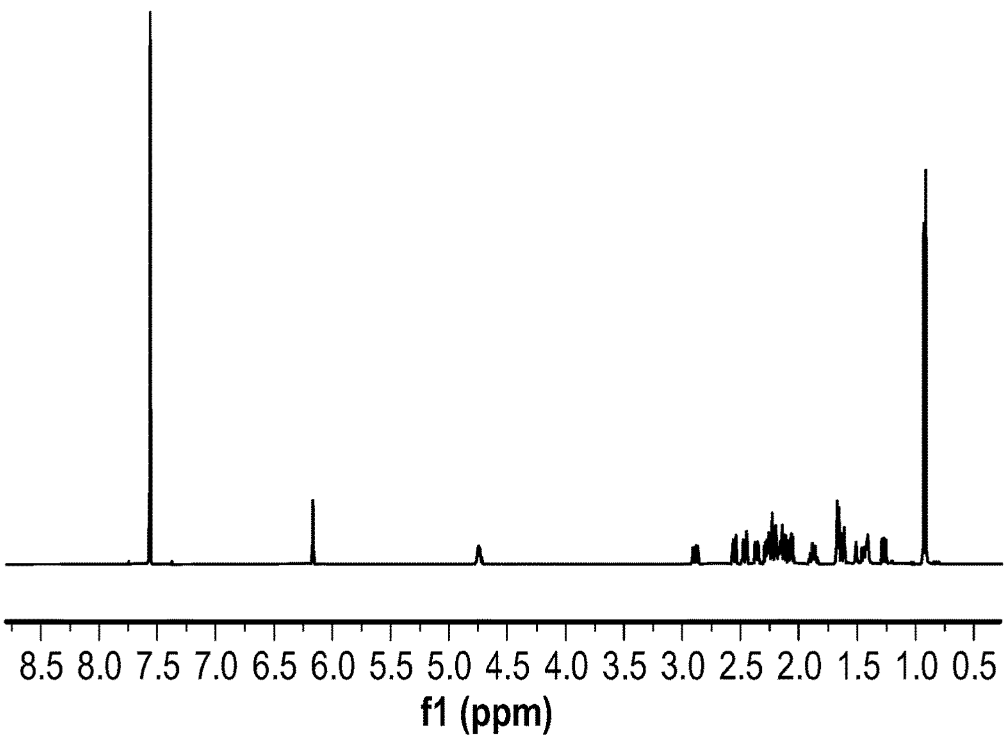
Figure 4:
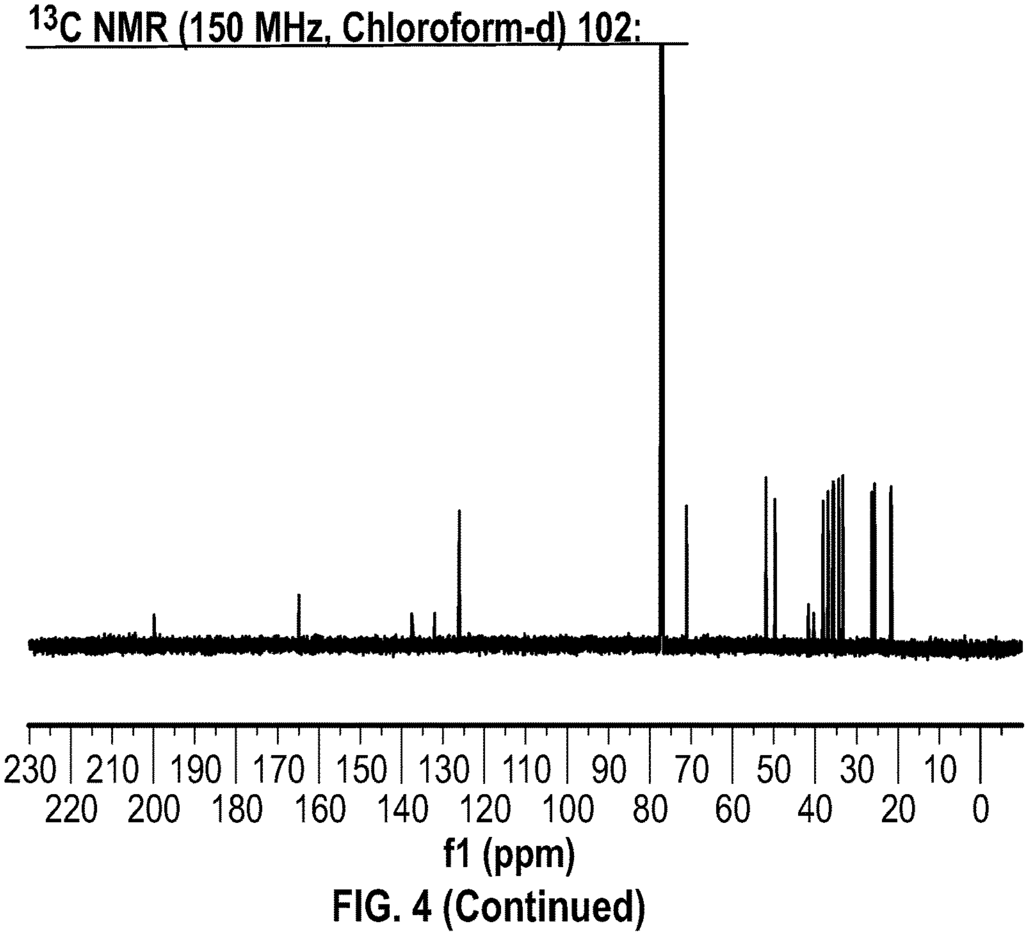
Figure 4:
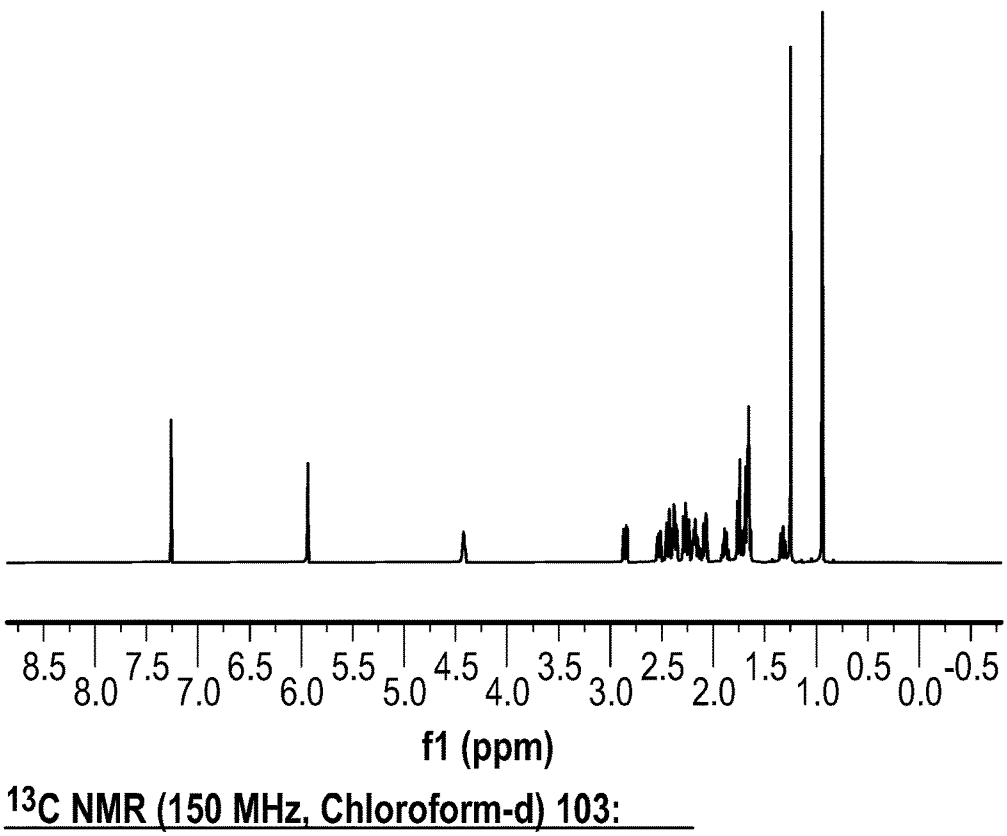
Figure 4:
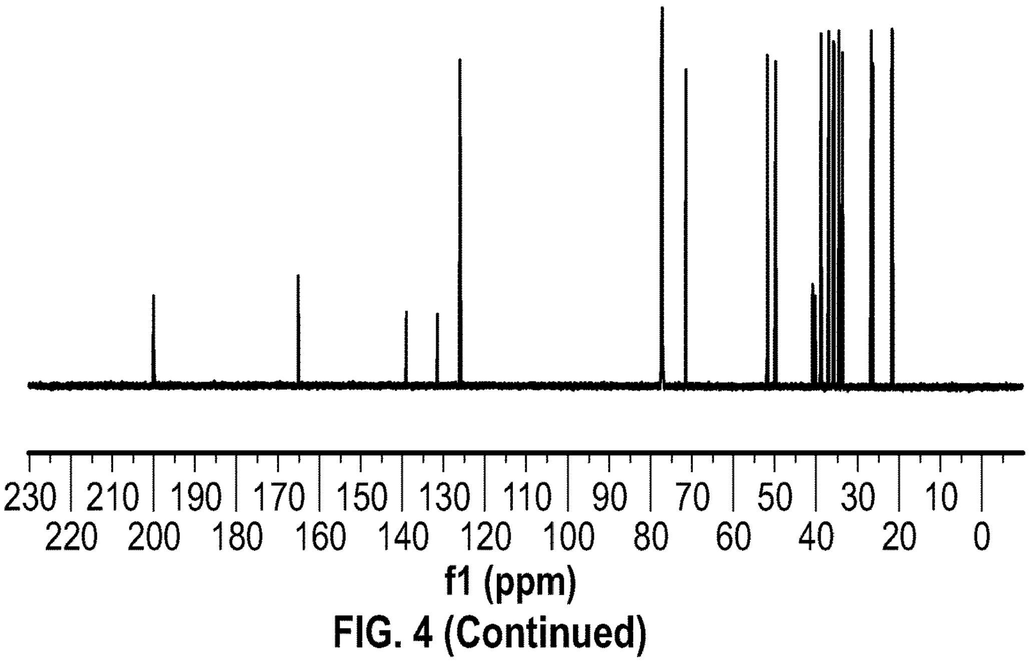
Figure 4:
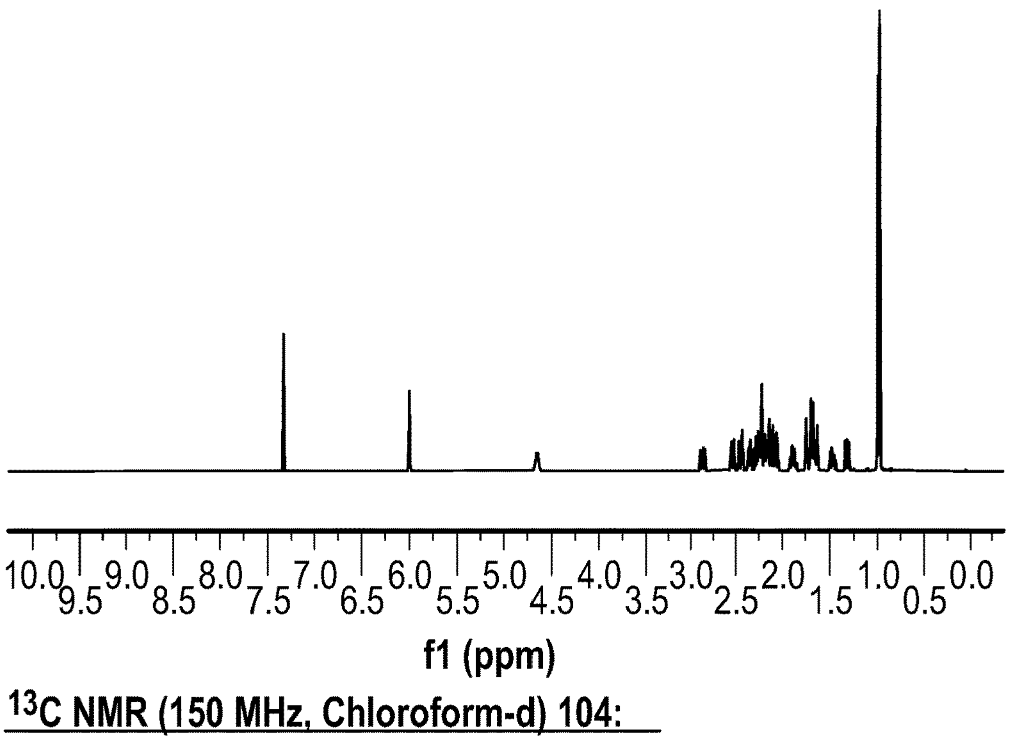
Figure 4:
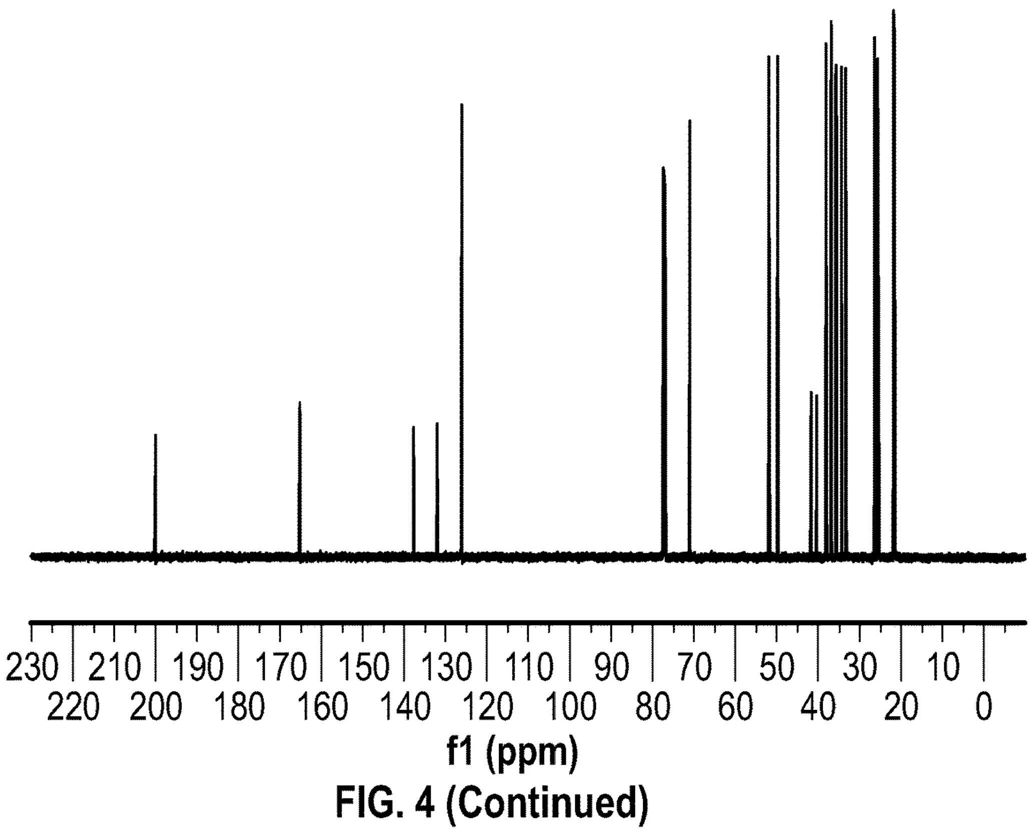
Figure 4:
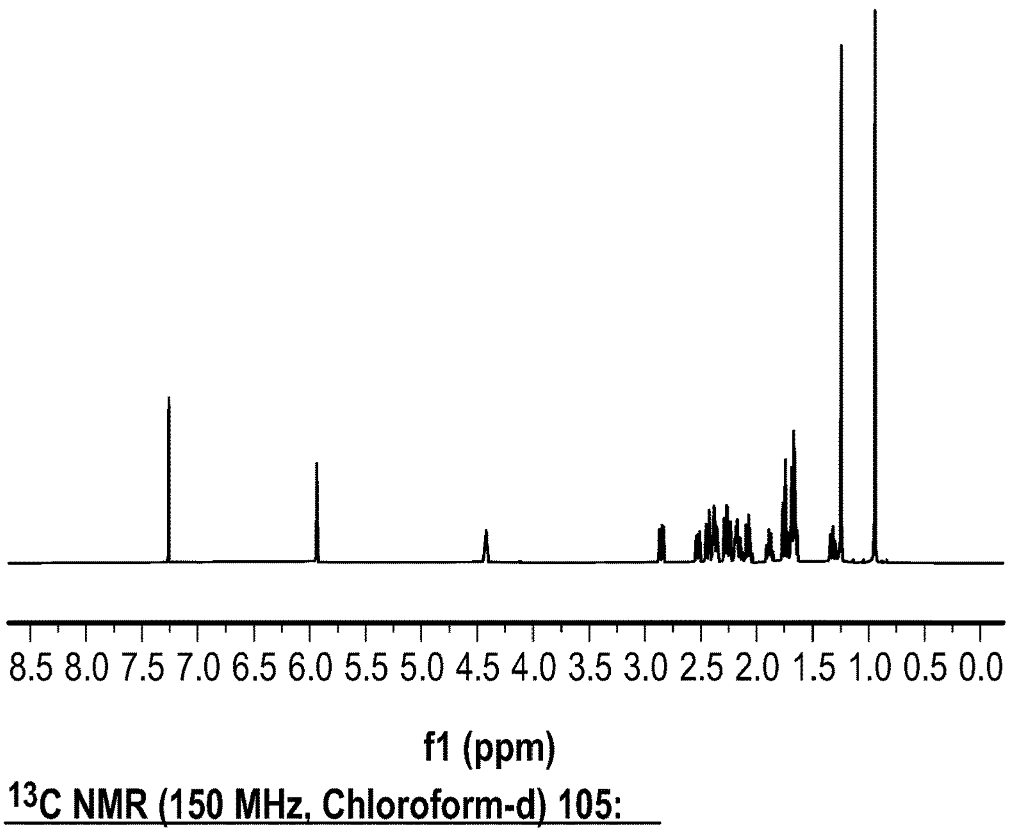
Figure 4:
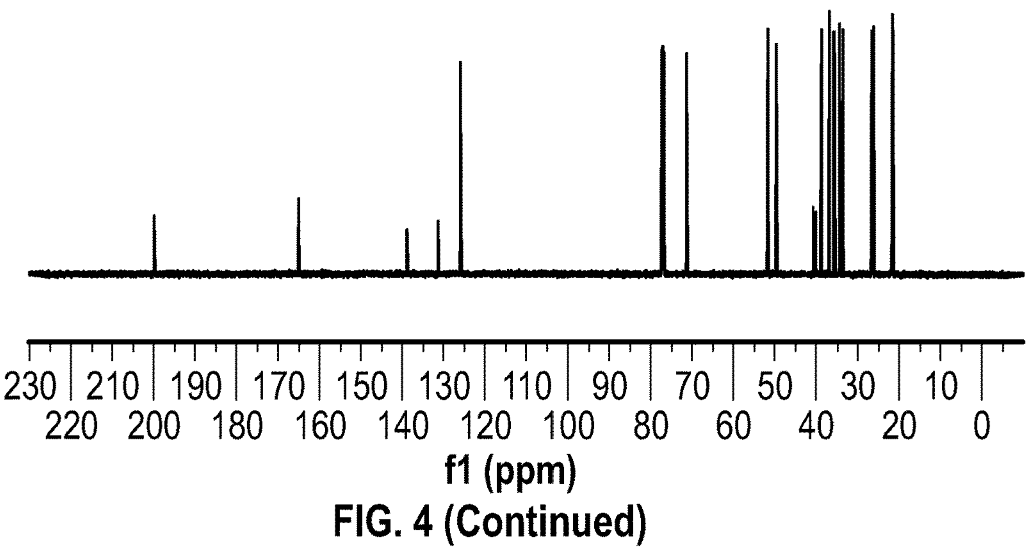
Figure 4:
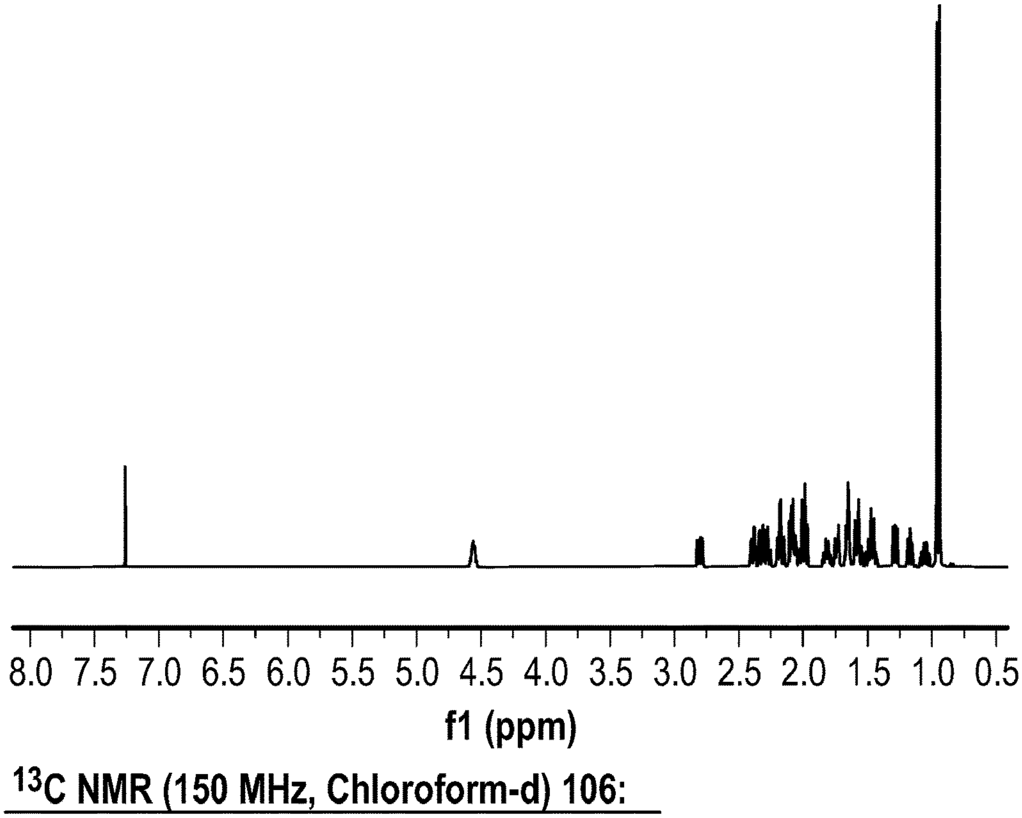
Figure 4:
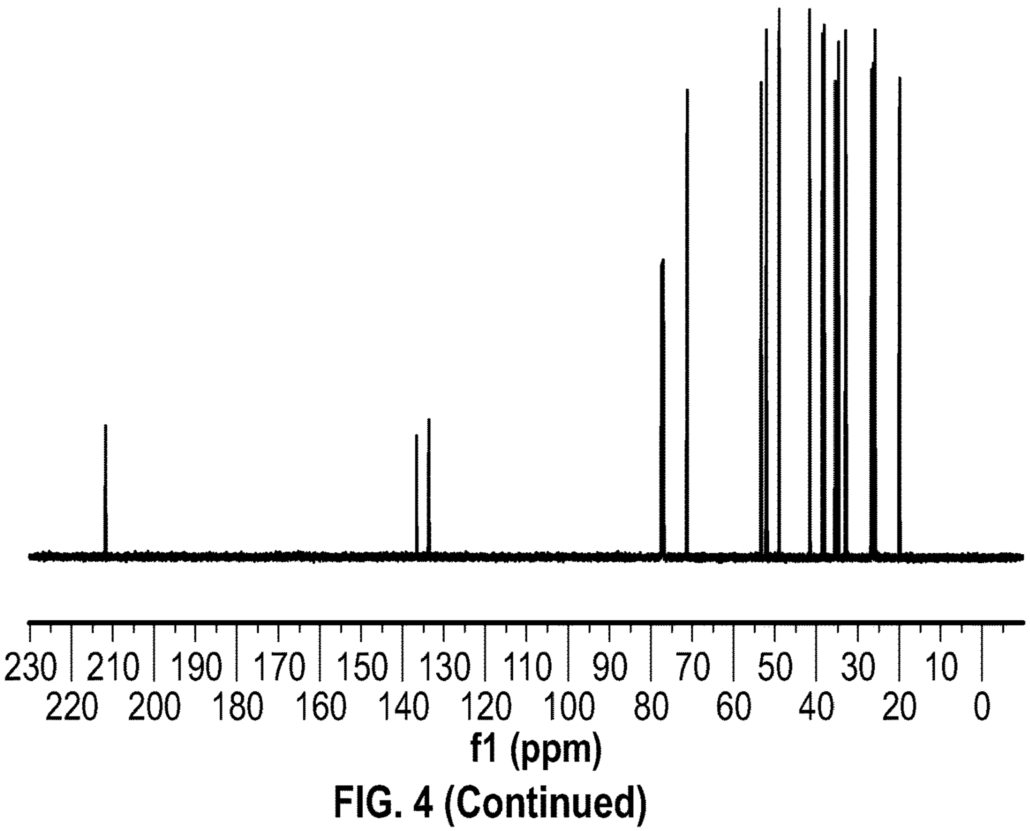
Figure 4:
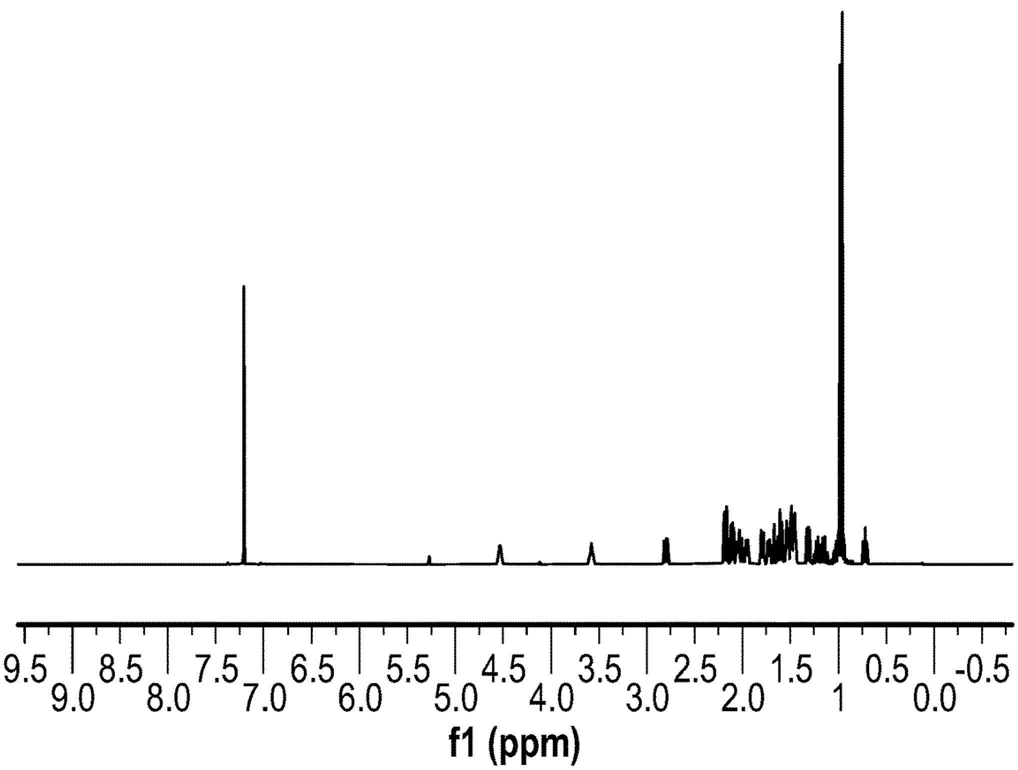
Figure 4:
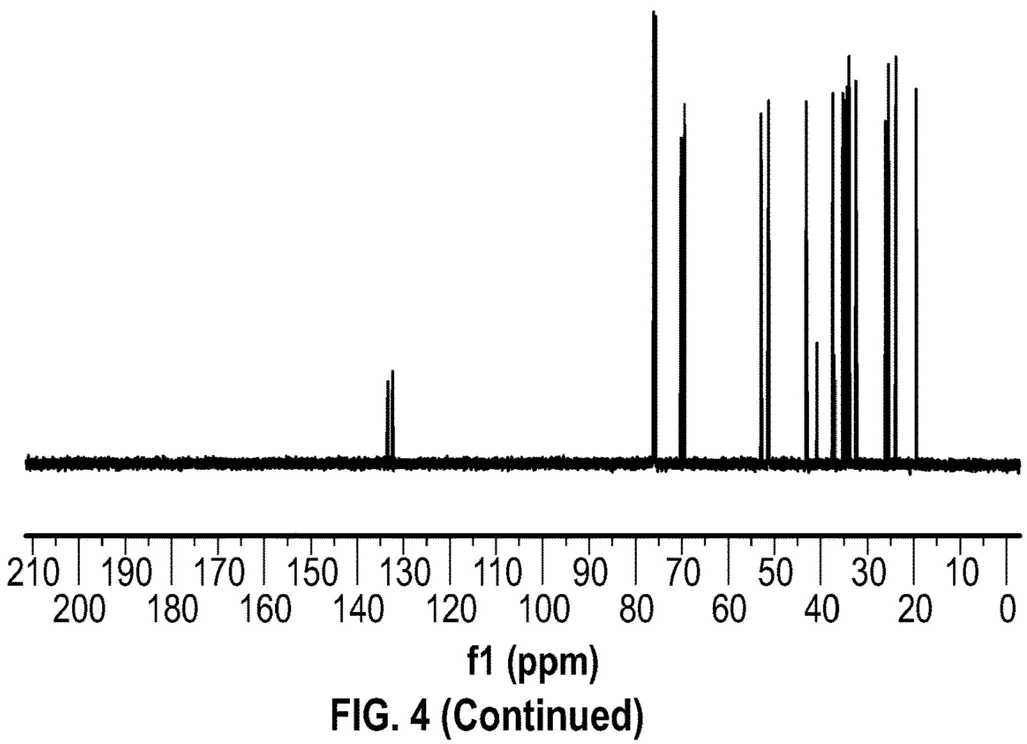
Figure 4:
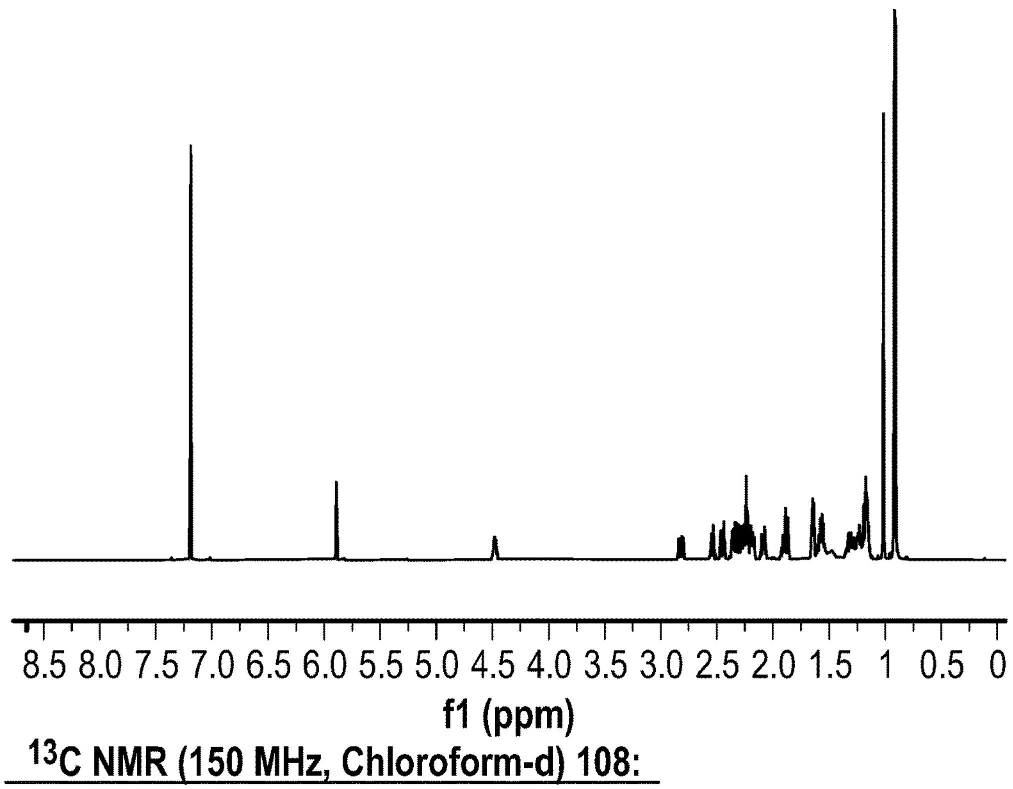
Figure 4:
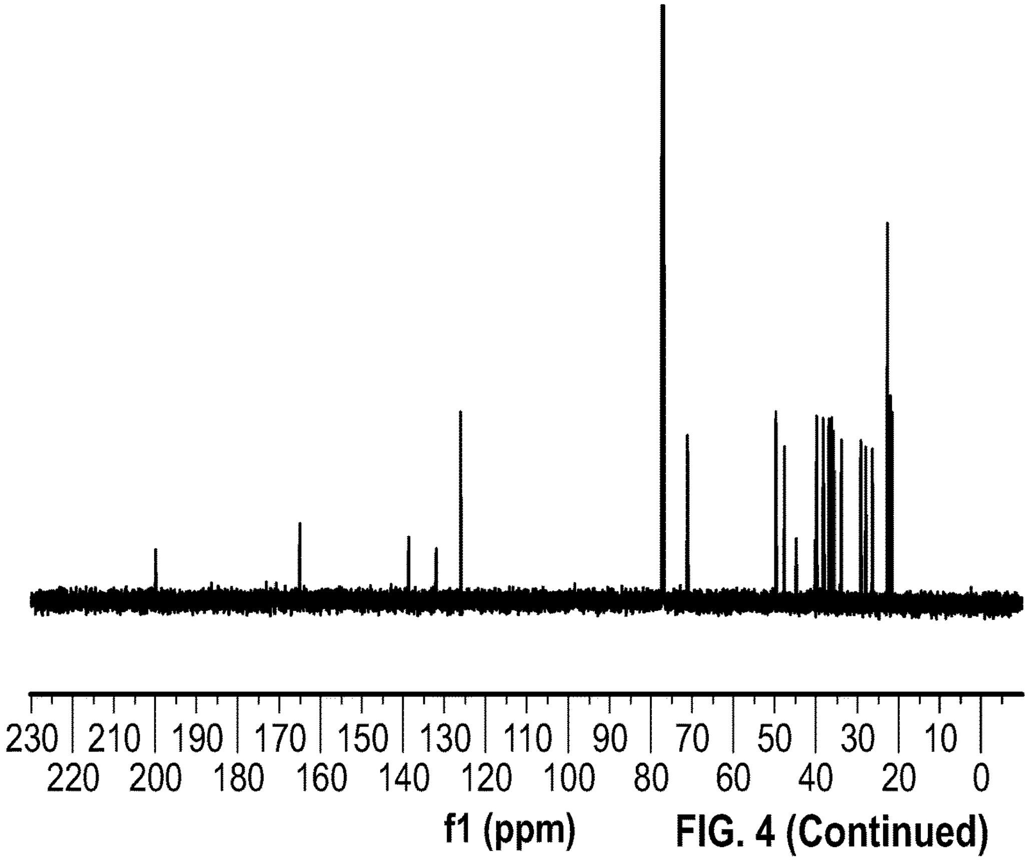
Figure 4:
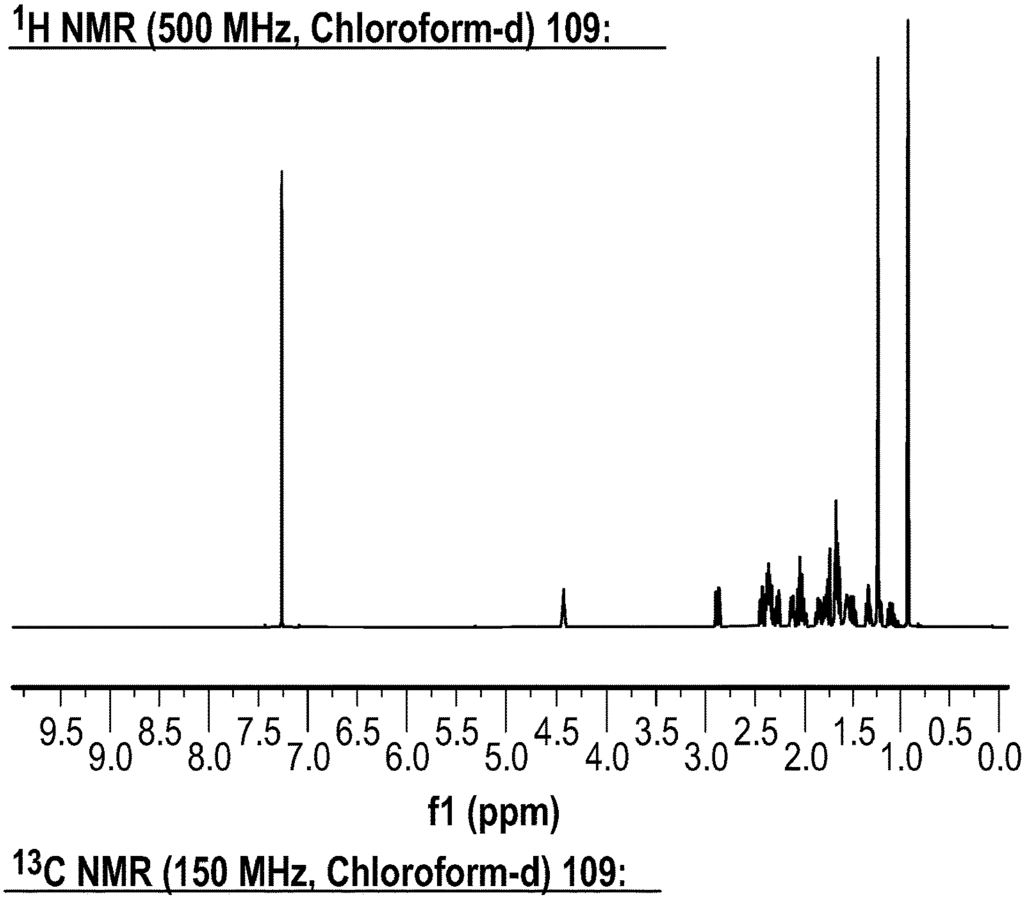
Figure 4:
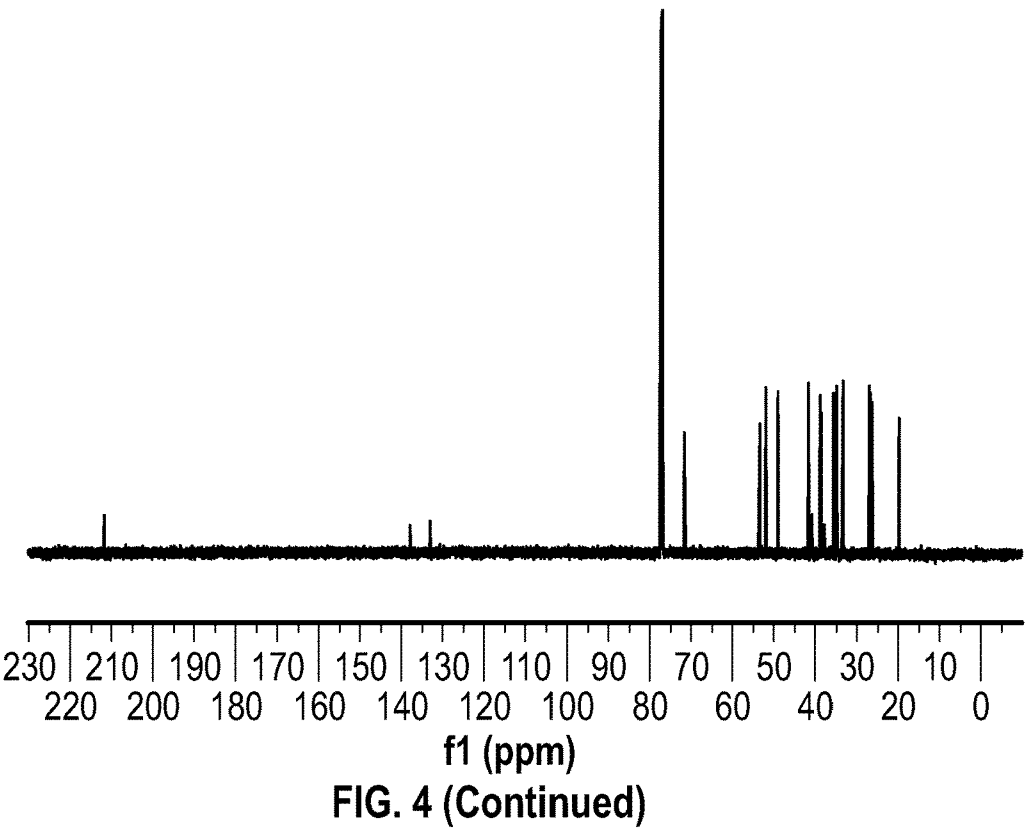
Figure 4:
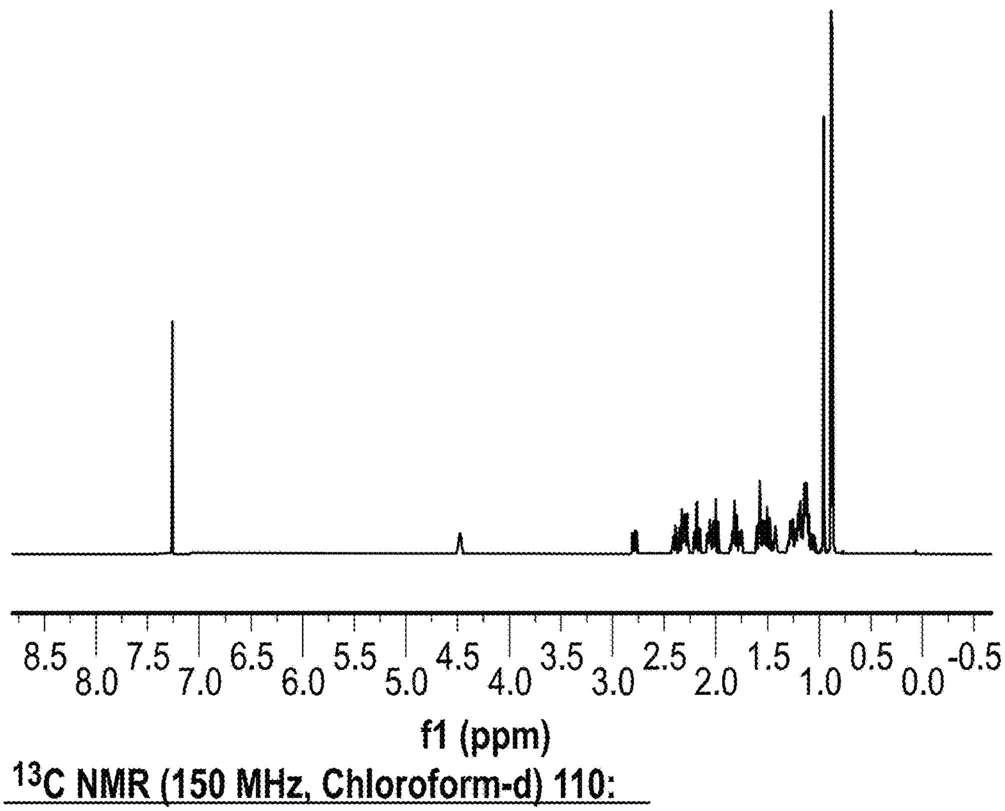
Figure 4:
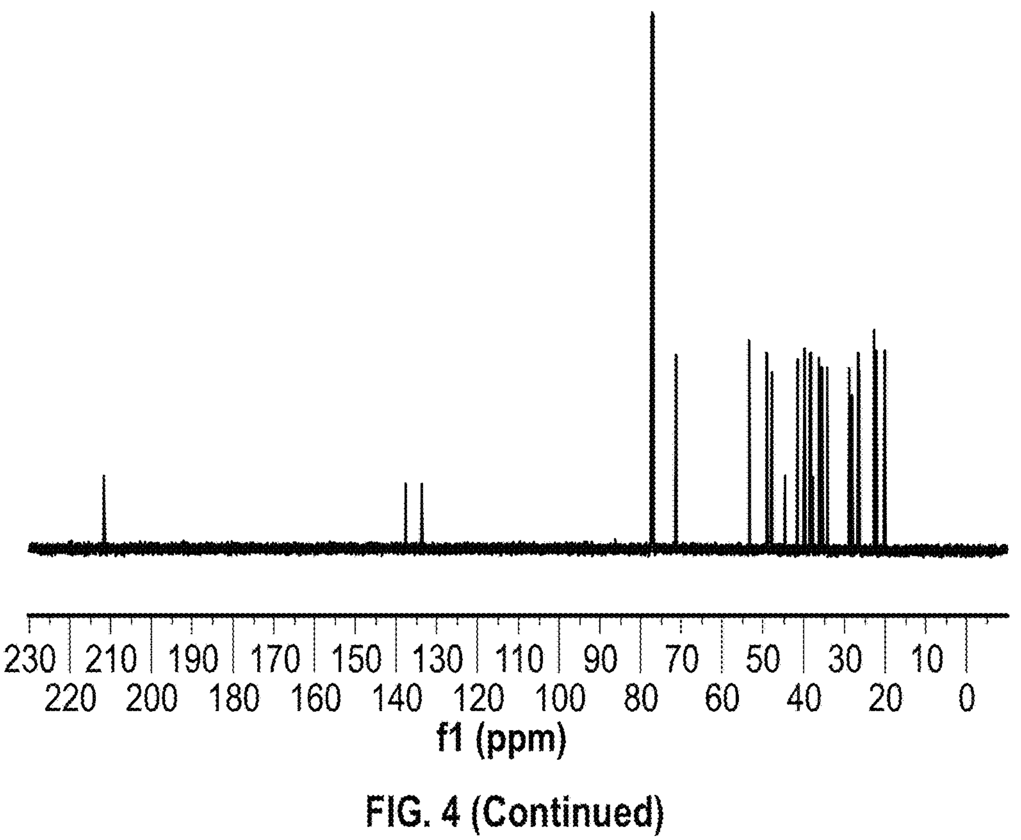

Compounds were characterized by nuclear magnetic resonance (NMR) spectroscopy. $^1H$ NMR and $^{13}C$ NMR spectra for Compounds 101-110 are shown in FIG. 4.

Example 2

Compound 202—(2S,2aR,3aR,5aS,9aS,11aR)-2-hydroxy-9a,11a-dimethyl-1,2a,3,4,5a,6,8,9,9a,10,11,11a-dodecahydro-2H-cyclopropa[1,5]cyclopenta[1,2-a] phenanthren-7(5H)-one Compound 202 was prepared in 3 steps from 17.

Preparation of Compound 201 from 17:

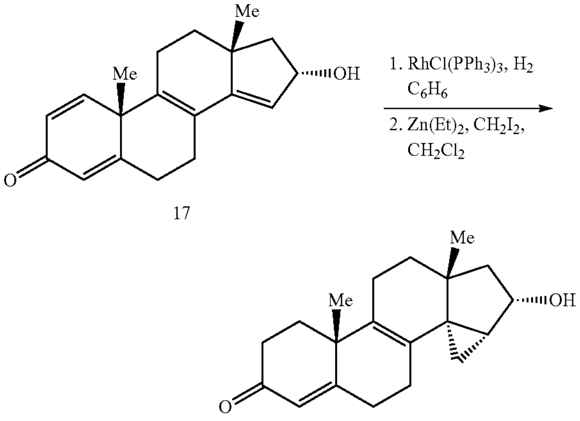

17

Compound 201

Dienone 17 is available in 7 steps from epichlorohydrin. See Kim et al., Nature Communications, 10, 2448 (2019).

The first step was a selective reduction of the C1-C2 alkene of dienone 17 and was accomplished through the following procedure: Diiodomethane (0.165 mL, 1.404 mmol, 6 equiv) was delivered dropwise to a stirred solution of 17 (65 mg, 0.233 mmol, 1 equiv) in $CH_2Cl_2$ (10 mL) cooled to 0° C. and allowed to stir for 2 minutes before adding $ZnEt_2$ (0.932 mL, 0.932 mmol, 4 equiv, 1 M in hexanes). The solution was allowed to warm to room temperature and stirred for two hours until quenched with 5 mL saturated aqueous $NH_4Cl$. The phases were separated, and the aqueous layer extracted with $CH_2Cl_2$ (4×10 mL). The combined organic extracts were dried over anhydrous $Na_2SO_4$, filtered and concentrated in vacuo then passed through a silica plug with 50% ethyl acetate/50% hexanes as an eluent to afford a white amorphous solid (43 mg).

The second step was a stereoselective cyclopropanation reaction and was accomplished through the following procedure: The crude isolate (43 mg) was dissolved in $C_6H_6$ (2.0 mL) to which $RhCl(PPh_3)_3$ (15 mg, 0.0162 mmol, 11 mol %) was added. The resulting solution was stirred under $H_2$ (1 atm) for 4 hours until the solvent was removed under reduced pressure. The crude isolate was purified by flash column chromatography on a Biotage cartridge using a gradient elution starting from 50% ethyl acetate/50% hexanes to 100% ethyl acetate to afford the title compound 201 (38 mg, 54% isolated yield over 2 steps) as a clear yellow film. $^1H$ NMR (600 MHZ, $C_6D_6$) δ 5.84 (s, 1H), 4.52-4.45 (m, 1H), 2.31-2.18 (m, 2H), 2.13-2.06 (m, 1H), 1.86-1.76 (m, 3H), 1.71-1.66 (m, 1H), 1.58-1.46 (m, 4H), 1.45-1.37 (m, 3H), 1.22 (br s, 1H), 0.93 (s, 3H), 0.87 (dd, J=12.6, 8.7 Hz, 1H), 0.81 (s, 3H), 0.68 (dd, J=4.9, 3.0 Hz, 1H), 0.11 (dd, J=7.8, 4.9 Hz, 1H). $^{13}C$ NMR (151 MHZ, $C_6D_6$) δ 196.6, 167.8, 132.4, 128.8, 123.7, 72.9, 41.3, 38.8, 38.7, 38.5, 34.3, 34.0, 31.5, 29.3, 27.1, 26.6, 23.0, 22.4, 21.0, 10.4. IR (neat, $cm^{-1}$) 3362, 2954, 2919, 1661, 1445, 1372, 1326, 1267, 1236, 1054, 1024, 863, 730, 700, 462 HRMS (ESI-TOF) m/z: [M+H]+ Calcd. for C20H27O2 299.2011; Found 299.2001; [α]589=+49.15 (c 0.22, $CHCl_3$).

Preparation of Compound 202 from Compound 201:

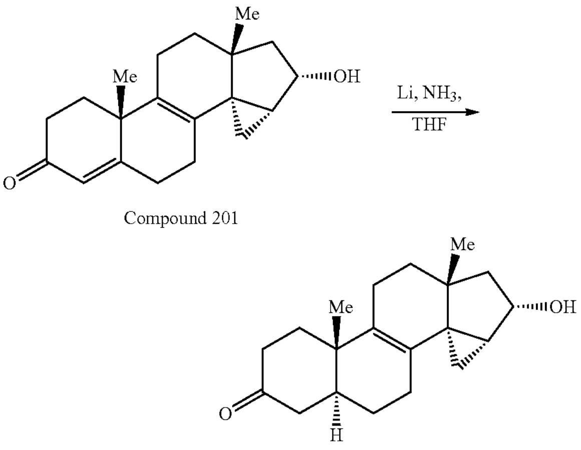

Compound 201

Compound 202

The third step was a chemo- and stereoselective dissolving metal reduction to reduce the C4-C5 alkene and generate Compound 202. $Li^0$ (35 mg, 5.39 mmol, 161 equiv) was added portion wise to a two-neck flask, equipped with a condensing Dewar, containing liquid $NH_3$ (I) (~10 mL) at ~78° C. The resulting dark blue solution was removed from the cold bath and refluxed at −28° C. for 30 min. The mixture was once again cooled to −78° C., and then a solution of Compound 201 in THF (1.5 mL) was added dropwise by syringe. The resulting mixture was stirred at −78° C. for 6 hours. After this time, the reaction was quenched by the gradual addition of saturated aqueous $NH_4Cl$. Once the blue color had dissipated, the flask was placed under a steady flow of $N_2$ (g) until all of the $NH_3$ (I) evaporated. The residue was diluted with water (10 mL) and $Et_2O$ (10 mL) and transferred to a separatory funnel. The phases were separated, and the aqueous layer extracted with $Et_2O$ (4×20 mL). The combined organic extracts were dried over anhydrous $Na_2SO_4$, filtered and concentrated in vacuo. The crude isolate was purified by flash column chromatography on a Biotage cartridge using a gradient elution starting from 35% ethyl acetate/65% hexanes to 100% ethyl acetate to afford the title compound 202 as a colorless clear film (6 mg, 60% isolated yield). $^1H$ NMR (600 MHZ, $C_6D_6$) δ 4.49-4.42 (m, 1H), 2.19 (ddt, J=15.4, 4.8, 2.2 Hz, 1H), 2.05 (ddd, J=14.8, 3.9, 2.2 Hz, 1H), 2.01-1.83 (m, 4H), 1.68 (dt, J=7.4, 3.6 Hz, 1H), 1.61-1.33 (m, 7H), 1.26-1.18 (m, 1H), 1.12 (td, J=13.4, 5.1 Hz, 1H), 1.00-0.94 (m, 1H), 0.88-0.84 (m, 1H), 0.82 (s, 3H), 0.76 (s, 3H), 0.63 (dd, J=4.8, 3.1 Hz, 1H), 0.18 (dd, J=7.7, 4.8 Hz, 1H). $^{13}C$ NMR (151 MHZ, $C_6D_6$) δ 208.4, 134.7, 73.5, 44.8, 42.8, 41.9, 39.1, 38.8, 38.2, 36.4, 36.2, 32.1, 27.2, 25.2, 25.1, 23.3, 22.4, 16.2, 10.5. IR (neat, $cm^{-1}$) 3394, 2950, 2924, 2870, 1710, 1449, 1414, 1375, 1337, 1278, 1184, 1132, 1057, 1024, 755, 734, 696, 674, 465

HRMS (ESI-TOF) m/z: [M+H]+ Calcd. for C20H29O2 301.2168; Found 301.2161; [α]589=−35.92 (c 0.15, $CHCl_3$).

Example 3

The activity of certain compounds were tested in a human AR agonist assay and a human AR antagonist assay (Indigo Biosciences).

Results from the human AR agonist assay for Compounds 101-103 are shown in FIG. 1 and Table 1.

TABLE 1

| | 6α-F testosterone | Compound 101 | Compound 102 | Compound 103 |
|---|---|---|---|---|
| HillSlope | 1.343 | 1.063 | 1.300 | ≈1.247 |
| EC50 (nM) | 0.02995 | 10029 | 23028 | ≈8948409 |

Figure 2:
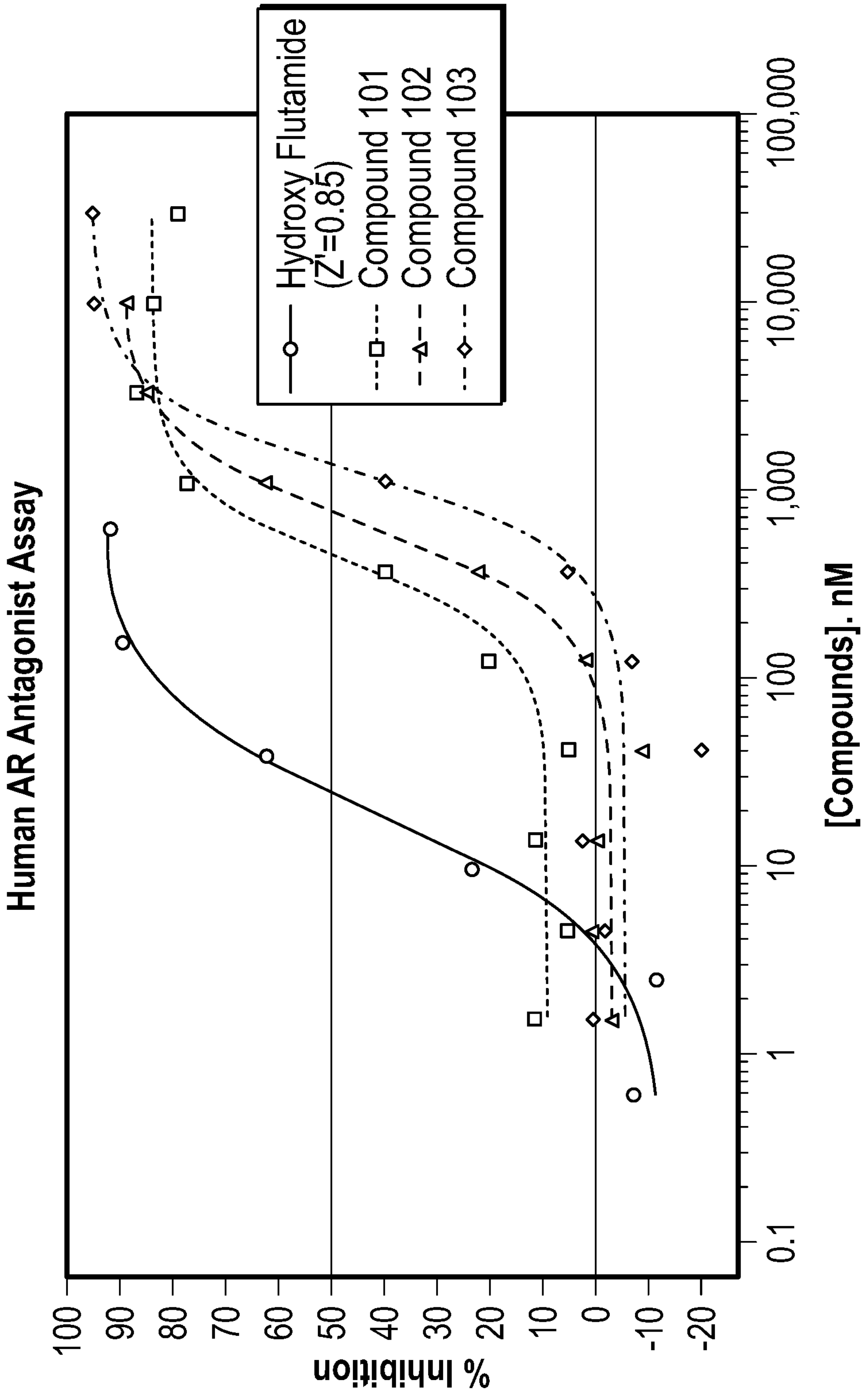
FIG. 2 is a line graph showing the results of a human AR antagonist assay for hydroxy flutamide and Compounds 101, 102, and 103.

Results from the human AR antagonist assay for Compounds 101-103 are shown in FIG. 2 and Table 2.

TABLE 2

| | hydroxyflutamide | Compound 101 | Compound 102 | Compound 103 |
|---|---|---|---|---|
| HillSlope | 1.305 | 2.100 | 1.728 | 1.906 |
| IC50 (nM) | 18.39 | 413.1 | 654.3 | 1243 |

Figure 3:
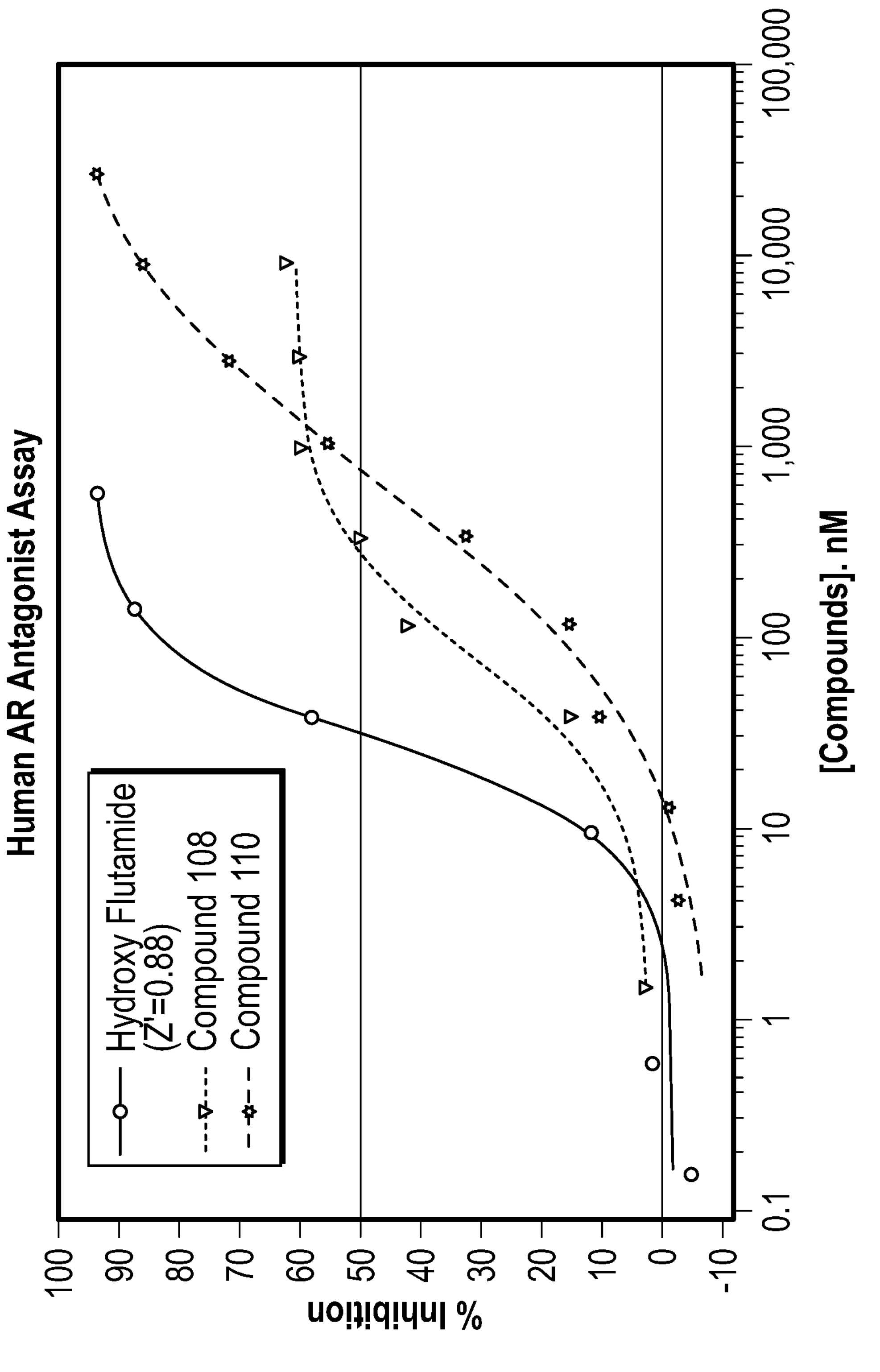
FIG. 3 is a line graph showing the results of a human AR antagonist assay for hydroxy flutamide and Compounds 108 and 110.

Results from the human AR antagonist assay for Compounds 108 and 110 are shown in FIG. 3 and Table 3.

TABLE 3

| | Compound | | |
|---|---|---|---|
| | hydroxyflutamide | 108 | 110 |
| HillSlope | 1.653 | 1.225 | 0.6338 |
| IC50 (nM) | 29.16 | 84.17 | 696.2 |

Figure 5:
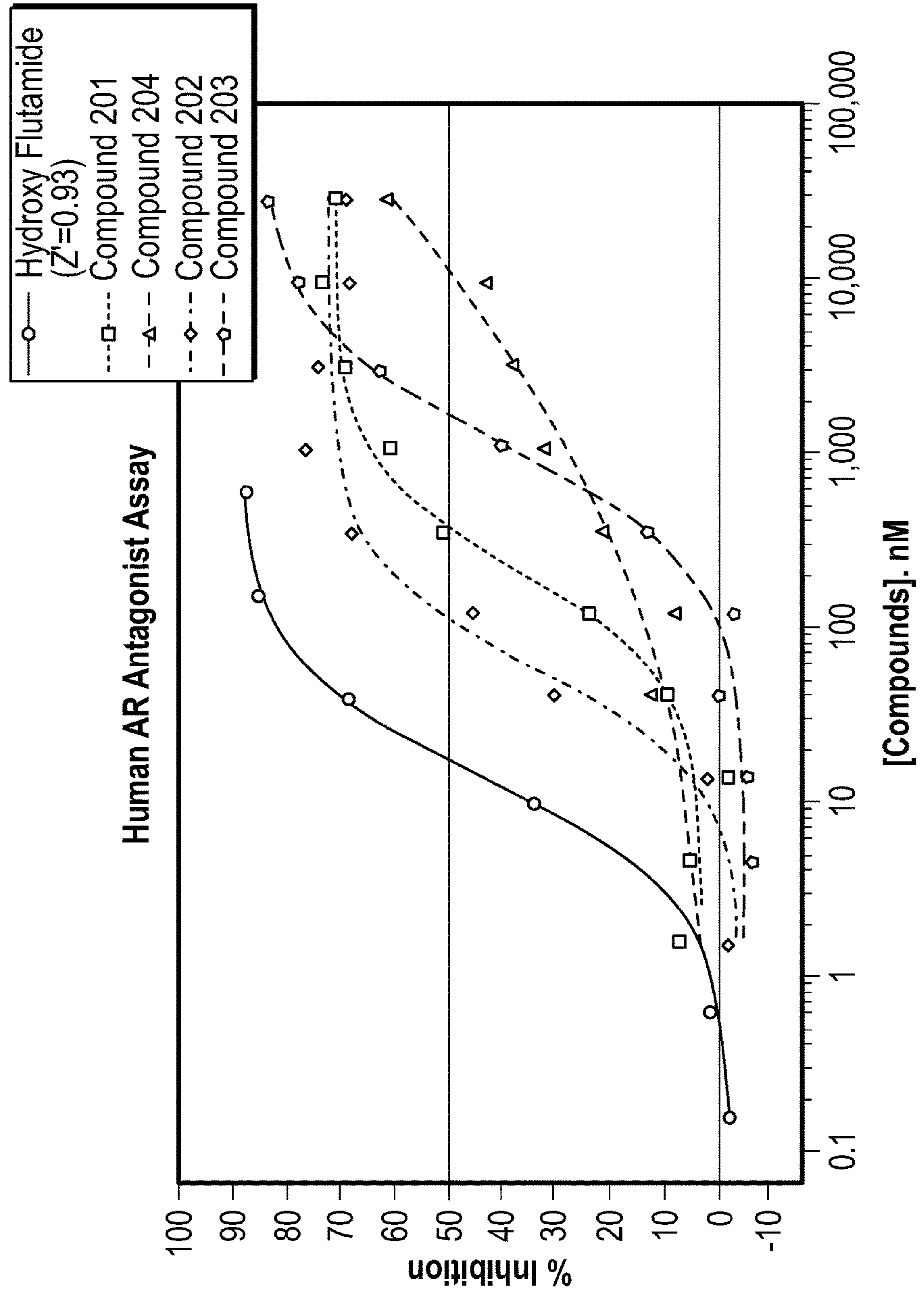
FIG. 5 is a line graph showing the results of a human AR antagonist assay for hydroxy flutamide and Compounds 201, 202, 203, and 204.

Results from the human AR antagonist assay for Compounds 201, 202, and 203 are shown in FIG. 5 and Table 4.

TABLE 4

| | Compound | | | |
|---|---|---|---|---|
| | hydroxyflutamide | 201 | 202 | 203 |
| HillSlope | 1.282 | 1.375 | 1.360 | 1.202 |
| IC50 (nM) | 13.77 | 218.0 | 60.53 | 1180 |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicant reserves the right to challenge the accuracy and pertinence of the cited references.

What is claimed is:

1. A compound or pharmaceutically acceptable salt thereof, wherein the compound has a structure corresponding to Formula (VII-A) or Formula (VII-D):

(VII-A)

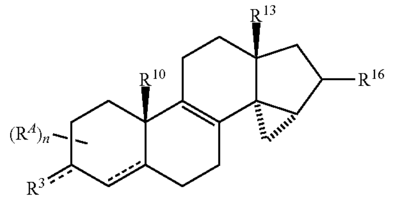

-continued (VII-D)

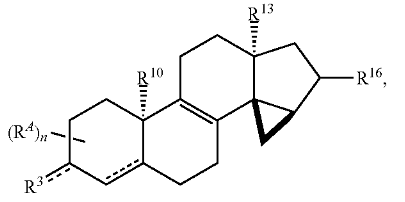

wherein n is an integer selected from the group consisting of 0, 1, 2, 3, 4, 5, and 6;

each $R^A$ is independently selected from the group consisting of hydrogen, $C_{1-10}$-alkyl, $C_{2-10}$-alkenyl, $C_{2-10}$-alkynyl, $C_{1-10}$-haloalkyl, halogen, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl, wherein $R^{AX}$ is hydrogen, $C_{1-6}$-alkyl, $C_{2-10}$-alkenyl, $C_{2-10}$-alkynyl, $C_{1-10}$-haloalkyl, —C(O)—$C_{1-10}$-alkyl, —C(O)—$C_{6-10}$-aryl, —C(O)-heteroaryl, —C(O)—O—$C_{1-10}$-alkyl, —C(O)—O—$C_{6-10}$-aryl, —C(O)—O-heteroaryl, —C(O)—$NR^{Z1}R^{Z2}$, —$S(O)_2NR^{Z1}R^{Z2}$, —$S(O)_2R^{Z1}$, $C_{6-10}$-aryl, or 5- to 10-membered heteroaryl, wherein $R^{AY}$ is hydrogen, $C_{1-6}$-alkyl, $C_{2-10}$-alkenyl, $C_{2-10}$-alkynyl, $C_{1-10}$-haloalkyl, —C(O)—$C_{1-10}$-alkyl, —C(O)—$C_{6-10}$-aryl, —C(O)-heteroaryl, $C_{6-10}$-aryl, or 5- to 10-membered heteroaryl, wherein each of $R^{Z1}$ and $R^{Z2}$ are independently hydrogen, $C_{1-6}$-alkyl, $C_{2-10}$-alkenyl, $C_{2-10}$-alkynyl, $C_{1-10}$-haloalkyl, —$(CH_2)_m$—$C_{6-10}$-aryl, —$(CH_2)_m$-5- to 10-membered heteroaryl, hydroxy, or $C_{1-6}$-alkoxy:

$R^3$ is oxo or —$OR^{3X}$, wherein $R^{3X}$ is hydrogen or $C_{1-6}$-alkyl;

$R^{10}$ is selected from the group consisting of $C_{1-10}$-alkyl, $C_{2-10}$-alkenyl, $C_{2-10}$-alkynyl, $C_{1-10}$-haloalkyl, $—(CH_2)_m—C_{6-10}$-aryl, and $—(CH_2)_m$-5- to 10-membered heteroaryl;

$R^{13}$ is selected from the group consisting of $C_1$-$C_{14}$-alkyl, $C_1$-$C_{14}$-haloalkyl, $C_2$-$C_{14}$-alkenyl, $C_2$-$C_{14}$-haloalkenyl, $C_2$-$C_{14}$-alkynyl, $C_2$-$C_{14}$-haloalkynyl, each of which is optionally interrupted by one or more of —O—, $—NR^Z—$, —C(O)—, —C(O)O—, —OC(O)—, $—C(O)NR^Z—$, $—NR^ZC(O)—$, $—S(O)_y—$, $—S(O)_yNR^Z—$, $—NR^ZS(O)_y—$, $—C(S)NR^Z—$, $—NR^ZC(S)—$, $—(CH_2)_m—C_{6-10}$-aryl, and $—(CH_2)_m$-5- to 10-membered heteroaryl;

$R^{16}$ is $—OR^D$ and $R^D$ is selected from the group consisting of hydrogen, $C_{1-10}$-alkyl, $C_{1-10}$-haloalkyl, $—C(O)—C_{1-10}$-alkyl, and $—C(O)—C_{1-10}$-haloalkyl; and each - - - independently represents a single bond or a double bond;

m is an integer selected from the group consisting of 0, 1, 2, and 3;

wherein any $C_{6-10}$-aryl or 5- to 10-membered heteroaryl is optionally substituted with one or more halogen, hydroxy, $C_{1-6}$-alkyl, $C_{1-6}$-haloalkyl, or $C_{1-6}$-alkoxy.

2. The compound or pharmaceutically acceptable salt of claim 1, wherein $R^{10}$ is selected from the group consisting of $C_{1-10}$-alkyl, $C_{2-10}$-alkenyl, $C_{2-10}$-alkynyl, $C_{1-10}$-haloalkyl, $—(CH_2)_m—C_{6-10}$-aryl, and $—(CH_2)_m$-5- to 10-membered heteroaryl.

3. The compound or pharmaceutically acceptable salt of claim 1, wherein $R^{10}$ is $C_{1-10}$-alkyl.

4. The compound or pharmaceutically acceptable salt of claim 1, wherein $R^{13}$ is $C_{1-10}$-alkyl.

5. The compound or pharmaceutically acceptable salt of claim 1, wherein $R^{16}$ is $—OR^D$ and $R^D$ is selected from the group consisting of hydrogen, $C_{1-10}$-alkyl, $C_{1-10}$-haloalkyl, $—C(O)—C_{1-10}$-alkyl, and $—C(O)—C_{1-10}$-haloalkyl.

6. The compound or pharmaceutically acceptable salt of claim 1, wherein $R^{10}$ is $C_{1-10}$-alkyl; $R^{13}$ is $C_{1-10}$-alkyl; and $R^{16}$ is oxo, —OH, or $—O—C(O)—C_{1-10}$-alkyl.

7. A compound or pharmaceutically acceptable salt thereof, wherein the compound has a structure corresponding to:

201

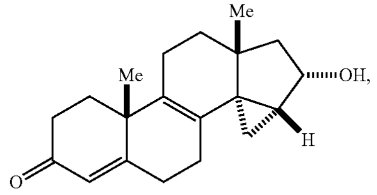

202

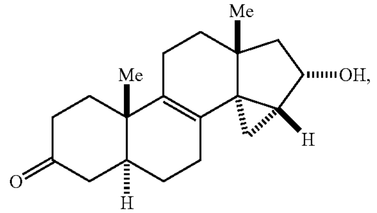

-continued

203

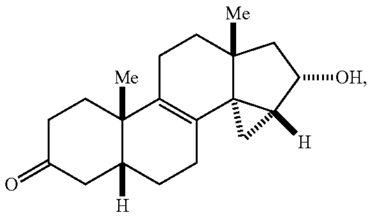

or

204

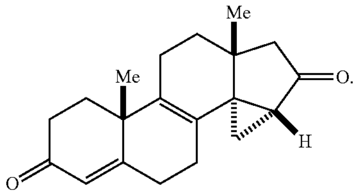

8. A method for treating a disease associated with androgen receptor activity in a subject in need thereof, the method comprising administering to the subject a therapeutically effective amount of a compound of claim 1 or pharmaceutically acceptable salt or prodrug thereof.

9. A method for treating a disease associated with androgen receptor activity in a subject in need thereof, the method comprising administering to the subject a therapeutically effective amount of a compound of claim 7, or pharmaceutically acceptable salt or prodrug thereof.

10. The method of claim 9, wherein the diseases associated with androgen receptor activity is cancer (e.g., prostate cancer, preferably castration-resistant prostate cancer), benign prostatic hyperplasia, hypersexuality, acne, amenorrhea, seborrhea, hirsutism, androgenic alopecia, hidradenitis suppurativa, or hyperandrogenism.

11. A pharmaceutical composition comprising (i) a compound of claim 7, or pharmaceutically acceptable salt or prodrug thereof and (ii) a pharmaceutically acceptable excipient.

12. A composition comprising a compound of claim 7, or pharmaceutically acceptable salt or prodrug thereof, wherein the composition has not more than 15% of an enantiomeric impurity.

13. A composition comprising a compound of any one of claim 7, or pharmaceutically acceptable salt or prodrug thereof, wherein the composition has not more than 15% of an enantiomeric impurity.

14. A compound or pharmaceutically acceptable salt thereof, wherein the compound has a structure corresponding to Formula (VII-A):

(VII-A)

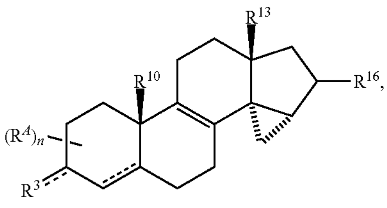

wherein n is an integer selected from the group consisting of 0, 1, 2, 3, 4, 5, and 6;

each $R^A$ is independently selected from the group consisting of hydrogen, $C_{1-10}$-alkyl, $C_{2-10}$-alkenyl, $C_{2-10}$-alkynyl, $C_{1-10}$-haloalkyl, halogen, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl, wherein $R^{AX}$ is hydrogen, $C_{1-6}$-alkyl, $C_{2-10}$-alkenyl, $C_{2-10}$-alkynyl, $C_{1-10}$-haloalkyl, —C(O)—$C_{1-10}$-alkyl, —C(O)—$C_{6-10}$-aryl, —C(O)-heteroaryl, —C(O)—O—$C_{1-10}$-alkyl, —C(O)—O—$C_{6-10}$-aryl, —C(O)—O-heteroaryl, —C(O)—$NR^{Z1}R^{Z2}$, —$S(O)_2NR^{Z1}R^{Z2}$, —$S(O)_2R^{Z1}$, $C_{6-10}$-aryl, or 5- to 10-membered heteroaryl, wherein $R^{AY}$ is hydrogen, $C_{1-6}$-alkyl, $C_{2-10}$-alkenyl, $C_{2-10}$-alkynyl, $C_{1-10}$-haloalkyl, —C(O)—$C_{1-10}$-alkyl, —C(O)—$C_{6-10}$-aryl, —C(O)-heteroaryl, $C_{6-10}$-aryl, or 5- to 10-membered heteroaryl, wherein each of $R^{Z1}$ and $R^{Z2}$ are independently hydrogen, $C_{1-6}$-alkyl, $C_{2-10}$-alkenyl, $C_{2-10}$-alkynyl, $C_{1-10}$-haloalkyl, —$(CH_2)_m$—$C_{6-10}$-aryl, —$(CH_2)_m$-5- to 10-membered heteroaryl, hydroxy, or $C_{1-6}$-alkoxy;

$R^3$ is oxygen or —$OR^{3X}$, wherein $R^{3X}$ is hydrogen or $C_{1-6}$-alkyl;

$R^{10}$ is selected from the group consisting of $C_{1-10}$-alkyl, $C_{2-10}$-alkenyl, $C_{2-10}$-alkynyl, $C_{1-10}$-haloalkyl, —$(CH_2)_m$—$C_{6-10}$-aryl, and —$(CH_2)_m$-5- to 10-membered heteroaryl;

$R^{13}$ is selected from the group consisting of $C_1$-$C_{14}$-alkyl, $C_1$-$C_{14}$-haloalkyl, $C_2$-$C_{14}$-alkenyl, $C_2$-$C_{14}$-haloalkenyl, $C_2$-$C_{14}$-alkynyl, $C_2$-$C_{14}$-haloalkynyl, each of which is optionally interrupted by one or more of —O—, —$NR^Z$—, —C(O)—, —C(O)O—, —OC(O)—, —C(O)$NR^Z$—, —$NR^Z$C(O)—, —$S(O)_y$—, —$S(O)_yNR^Z$—, —$NR^ZS(O)_y$—, —C(S)$NR^Z$—, —$NR^Z$C(S)—, —$(CH_2)_m$—$C_{6-10}$-aryl, and —$(CH_2)_m$-5- to 10-membered heteroaryl;

$R^{16}$ is —$OR^D$ and $R^D$ is selected from the group consisting of hydrogen, $C_{1-10}$-alkyl, $C_{1-10}$-haloalkyl, —C(O)—$C_{1-10}$-alkyl, and —C(O)—$C_{1-10}$-haloalkyl; and each ---- independently represents a single bond or a double bond;

m is an integer selected from the group consisting of 0, 1, 2, and 3;

wherein any $C_{6-10}$-aryl or 5- to 10-membered heteroaryl is optionally substituted with one or more halogen, hydroxy, $C_{1-6}$-alkyl, $C_{1-6}$-haloalkyl, or $C_{1-6}$-alkoxy.

15. The compound or pharmaceutically acceptable salt of claim 14, wherein $R^{10}$ is $C_{1-10}$-alkyl.

16. The compound or pharmaceutically acceptable salt of claim 14, wherein $R^{13}$ is $C_{1-10}$-alkyl.

17. The compound or pharmaceutically acceptable salt of claim 14, wherein $R^{10}$ is $C_{1-10}$-alkyl; $R^{13}$ is $C_{1-10}$-alkyl; and $R^{16}$ is —OH, or —O—C(O)—$C_{1-10}$-alkyl.

18. A method for treating a disease associated with androgen receptor activity in a subject in need thereof, the method comprising administering to the subject a therapeutically effective amount of a compound of claim 14 or pharmaceutically acceptable salt or prodrug thereof.

* * * * *